United States Patent
Yamada

(10) Patent No.: US 9,608,120 B2
(45) Date of Patent: Mar. 28, 2017

(54) IMAGE PICKUP UNIT AND IMAGE PICKUP DISPLAY SYSTEM

(71) Applicant: SONY CORPORATION, Tokyo (JP)

(72) Inventor: Yasuhiro Yamada, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 14/778,950

(22) PCT Filed: Feb. 27, 2014

(86) PCT No.: PCT/JP2014/001047
§ 371 (c)(1),
(2) Date: Sep. 21, 2015

(87) PCT Pub. No.: WO2014/155969
PCT Pub. Date: Oct. 2, 2014

(65) Prior Publication Data
US 2016/0049523 A1 Feb. 18, 2016

(30) Foreign Application Priority Data

Mar. 26, 2013 (JP) .................. 2013-063729
Jul. 17, 2013 (JP) .................. 2013-148273

(51) Int. Cl.
*H01L 27/146* (2006.01)
*H01L 29/786* (2006.01)
*H01L 29/423* (2006.01)
*H01L 29/49* (2006.01)
(Continued)

(52) U.S. Cl.
CPC ....... *H01L 29/78648* (2013.01); *G01N 23/04* (2013.01); *H01L 27/1237* (2013.01); *H01L 27/14601* (2013.01); *H01L 27/14658* (2013.01); *H01L 27/14692* (2013.01); *H01L 29/42384* (2013.01); *H01L 29/4908* (2013.01); *H01L 29/78603* (2013.01); *H01L 29/78672* (2013.01)

(58) Field of Classification Search
CPC .. H01L 27/14658; H04N 9/045; G01T 1/2018
See application file for complete search history.

(56) References Cited

U.S. PATENT DOCUMENTS 5,825,050 A * 10/1998 Hirakawa ......... H01L 29/66765
257/57
5,929,449 A * 7/1999 Huang .................. G01T 1/2928
250/208.1
(Continued)

FOREIGN PATENT DOCUMENTS

JP 2011-135561 A 7/2011

*Primary Examiner* — Kiho Kim
(74) *Attorney, Agent, or Firm* — Chip Law Group

(57) ABSTRACT

A semiconductor device including a substrate, at least one gate electrode, at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer, and a semiconductor layer disposed between at least a portion of the first silicon oxide layer and at least a portion of the second silicon oxide layer. Also, an image pick-up device and a radiation imaging device including the semiconductor device.

20 Claims, 19 Drawing Sheets

(51) Int. Cl.
*G01N 23/04* (2006.01)
*H01L 27/12* (2006.01)

(56) References Cited

U.S. PATENT DOCUMENTS

| | | | | |
|---|---|---|---|---|
| 2003/0213914 A1* | 11/2003 | Kobayashi | ............ | G01T 1/2018 250/370.09 |
| 2010/0072474 A1* | 3/2010 | Abe | .................. | H01L 23/49855 257/57 |
| 2010/0102314 A1* | 4/2010 | Miyairi | ............ | H01L 29/42384 257/43 |
| 2010/0283049 A1* | 11/2010 | Sato | .................. | H01L 29/78606 257/43 |
| 2011/0284854 A1* | 11/2011 | Endo | ................... | H01L 29/4908 257/59 |
| 2016/0049523 A1 | 2/2016 | Yamada | | |

\* cited by examiner

IMAGE PICKUP UNIT AND IMAGE PICKUP DISPLAY SYSTEM

CROSS REFERENCE TO RELATED APPLICATIONS

This application claims the benefits of Japanese Priority Patent Application JP 2013-63729 filed on Mar. 26, 2013 and Japanese Priority Patent Application JP 2013-148273 filed on Jul. 17, 2013, the entire contents of each of which are incorporated herein by reference.

TECHNICAL FIELD

The present disclosure relates to an image pickup unit that acquires radiation-based images, for example, and an image pickup display system that includes such an image pickup unit.

BACKGROUND ART

As image pickup units that incorporate a built-in photoelectric converter device for each pixel (image pickup pixel), various types of the units have been proposed. Examples of such image pickup units may include a so-called optical touch panel, a radiographic image pickup unit, and the like (for example, see PTL 1).

CITATION LIST

Patent Literature

[PTL 1]
JP 2011-135561

SUMMARY

Technical Problem

The image pickup unit as described above uses a thin-film transistor (TFT) as a switching device for reading out signal charges from each pixel, although may have a disadvantage of deterioration in reliability that is caused by degradation in characteristics of this TFT.

It is desirable to provide an image pickup unit capable of achieving high reliability by suppressing degradation in characteristics of a transistor, and an image pickup display system that includes such an image pickup unit.

Solution to Problem

Some embodiments are directed to a semiconductor device including a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer. The at least one gate electrode may include a first gate electrode and a second gate electrode, wherein the first gate electrode is nearer to the substrate than the second gate electrode. The semiconductor device may be a laminated structure wherein the substrate, the first gate electrode, the first silicon oxide layer, the semiconductor layer, the second insulating layer, and the second gate electrode are arranged in this order. A first portion of the first silicon oxide layer may be in physical contact with the semiconductor layer and a second portion of the first silicon oxide layer is in physical contact with the second silicon oxide layer. The semiconductor layer may be disposed between the first gate electrode and the second gate electrode. A first capacitance between the first gate electrode and the semiconductor layer may be less than or equal to a second capacitance between the second gate electrode and the semiconductor layer. In some embodiments, the at least one gate electrode comprises only a first gate electrode. The second silicon oxide layer may be nearer to the substrate than the first gate electrode. The semiconductor device may be a laminated structure wherein the substrate, the first silicon oxide layer, the semiconductor layer, the second insulating layer, and the first gate electrode are arranged in this order. The first gate electrode may be nearer to the substrate than the first silicon oxide layer. The semiconductor device may be a laminated structure wherein the substrate, the first gate electrode, the first silicon oxide layer, the semiconductor layer, and the second insulating layer, are arranged in this order. In some embodiments, the first silicon oxide layer is a portion of a first insulating layer, the first insulating layer comprising a first silicon nitride layer. The second silicon oxide layer may be a portion of a second insulating layer, the second insulating layer comprising a second silicon nitride layer. The second silicon oxide layer may be a portion of an insulating layer, the insulating layer comprising a silicon nitride layer. The semiconductor layer may include a low temperature polysilicon material. The semiconductor layer may include microcrystal silicon. The at least one gate electrode may include at least one material selected from the group consisting of molybdenum, titanium, aluminum, tungsten, and chromium.

Some embodiments are directed to an image pick-up device comprising: a plurality of pixels, each pixel comprising at least one semiconductor device, the semiconductor device comprising: a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer. The at least one gate electrode may include a first gate electrode and a second gate electrode, wherein the first gate electrode is nearer to the substrate than the second gate electrode.

Some embodiments are directed to a radiation imaging apparatus comprising: a radiation source configured to emit radiation; and an image pick-up device configured to receive and detect at least a portion of the emitted radiation, the image pick-up device comprising a plurality of pixels, each pixel comprising at least one semiconductor device, the semiconductor device comprising: a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer.

Advantageous Effects of Invention

According to the image pickup unit and the image pickup display system of the above-described respective embodiments of the present disclosure, a transistor for reading out radiation-based signal charges from each pixel has a first silicon oxide film, a semiconductor layer including an active layer and a second silicon oxide film, and a first gate electrode arranged in opposition to the semiconductor layer with the first or second silicon oxide film interposed between, which are laminated in this order from a substrate side. The second silicon oxide film is smaller in thickness than the first silicon oxide film, which makes it possible to alleviate any influence of a state of an interface of the second silicon oxide film side on the semiconductor layer. As a result, this allows to achieve high reliability by suppressing degradation in characteristics of the transistor.

It is to be understood that both the foregoing general description and the following detailed description are exemplary, and are intended to provide further explanation of the technology as claimed.

BRIEF DESCRIPTION OF DRAWINGS

The accompanying drawings are included to provide a further understanding of the technology, and are incorporated in and constitute a part of this specification. The drawings illustrate embodiments and, together with the specification, serve to explain the principles of the technology.

DESCRIPTION OF EMBODIMENTS

Hereinafter, some embodiments of the present disclosure are described in details with reference to the attached drawings. It is to be noted that the descriptions are provided in the order given below.

1. Embodiment (an example of an image pickup unit where a silicon oxide film at a semiconductor layer side on a second gate insulating film is made smaller in thickness than a silicon oxide film on a first gate insulating film)
2. Modification Example 1 (an example of a transistor having a second gate insulating film of another laminated structure)
3. Modification Example 2 (an example of a transistor having a second gate insulating film of still another laminated structure)
4. Modification Example 3 (an example of a top-gate type transistor)
5. Modification Example 4 (an example of a bottom-gate type transistor)
6. Modification Example 5 (an example of another pixel circuit of a passive type)
7. Modification Example 6 (an example of still another pixel circuit of a passive type)
8. Modification Examples 7-1 and 7-2 (examples of a pixel circuit of an active type)
9. Modification Examples 8-1 and 8-2 (examples of indirect-conversion type and direct-conversion type radiographic image pickup units)
10. Application Example (an example of an image pickup display system)

(Embodiment)
(Overall Configuration of Image Pickup Unit 1)

Figure 1:
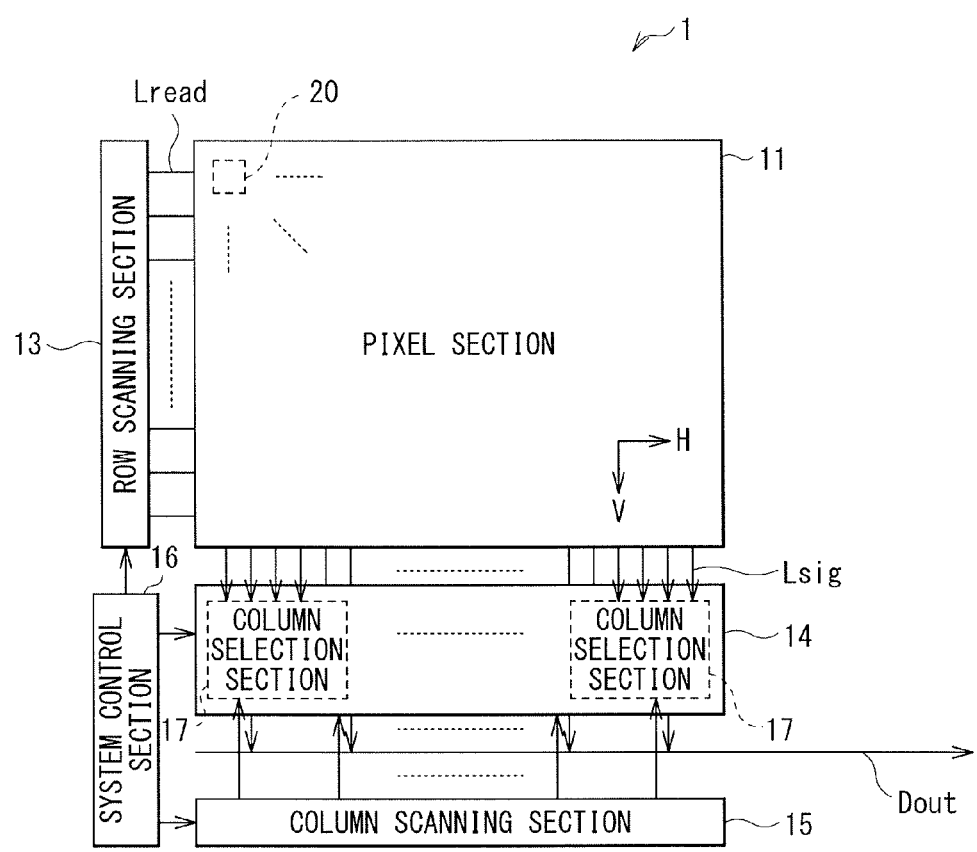
FIG. 1 is a schematic block diagram showing an overall configuration example of an image pickup unit according to an embodiment of the present disclosure.

FIG. 1 shows an overall block configuration of an image pickup unit (image pickup unit 1) according to an embodiment of the present disclosure. The image pickup unit 1 may read out information of a subject (pick up an image of a subject) based on incoming radiation, for example. The image pickup unit 1 includes a pixel section 11, as well as a row scanning section 13, an A/D conversion section 14, a column scanning section 15, and a system control section 16 as a driving circuit for the pixel section 11.

(Pixel Section 11)

The pixel section 11 generates signal charges based on radiation. On this pixel section 11, pixels (image pickup pixels, unit pixels) 20 are arranged two-dimensionally in a matrix pattern, and each of the pixels 20 has a photoelectric converter device (photoelectric converter device 21 to be hereinafter described) that generates photoelectric charges (signal charges) of the charge amount according to the amount of incident light (light-receiving amount), for example. It is to be noted that, as shown in FIG. 1, the description is hereinafter provided by denoting a horizontal direction (row direction) within the pixel section 11 as an "H" direction, and a vertical direction (column direction) as a "V" direction. Further, it is to be noted that, at a light incident side of the pixel section 11, there may be formed, for example, a wavelength conversion layer to be hereinafter described (wavelength conversion layer 112 in a modification example 8-1), where radiation may be converted into, for example, visible light, which enters the pixel section 11.

Figure 2:
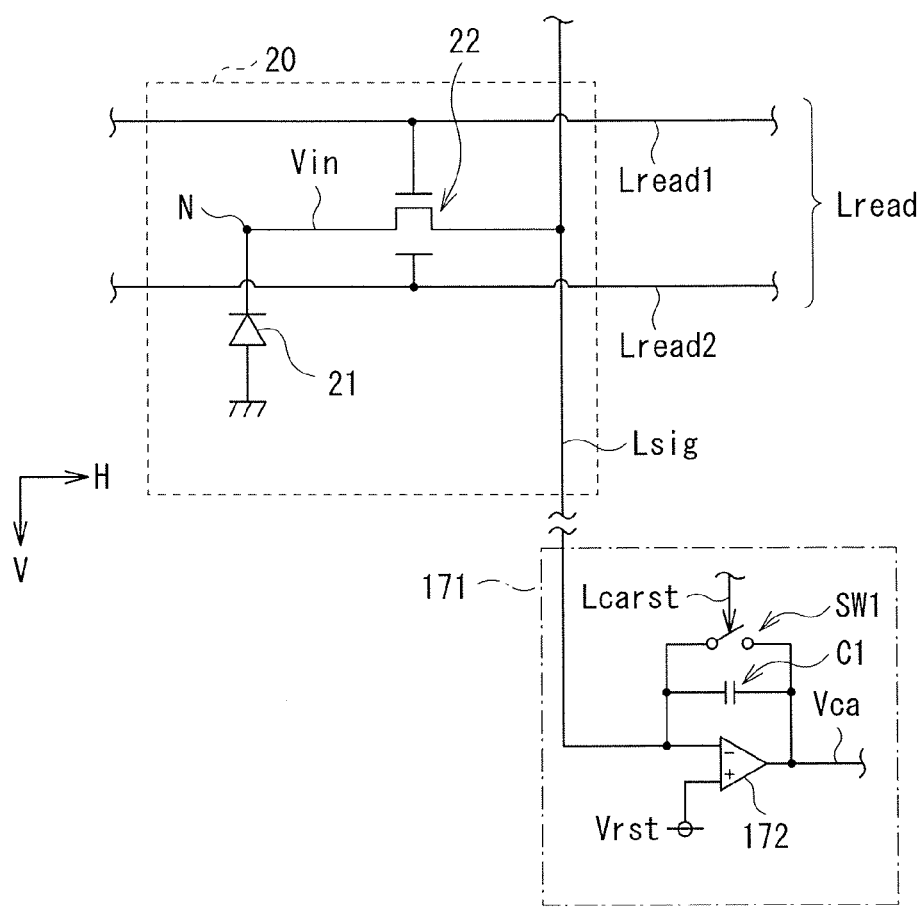
FIG. 2 is a circuit diagram showing a detailed configuration example of a pixel and the like illustrated in FIG. 1.

FIG. 2 shows a circuit configuration of the pixel 20 (circuit configuration of a so-called passive type) along with a circuit configuration of a column selection section 17 to be hereinafter described within the A/D conversion section 14. On this passive-type pixel 20, there are provided one photoelectric converter device 21 and one transistor 22. Further, a readout control line Lread (more specifically, including two readout control lines Lread1 and Lread2 to be hereinafter described) that extends along the H direction and a signal line Lsig that extends along the V direction are connected with the pixel 20.

The photoelectric converter device 21, which may be composed of, for example, a PIN (Positive Intrinsic Negative) type photodiode or an MIS (Metal-Insulator-Semiconductor) type sensor, generates signal charges of the charge amount according to the amount of incident light as described above. It is to be noted that a cathode of the photoelectric converter device 21 is connected with a storage node N in this example.

The transistor 22 is a transistor (readout transistor) to output a signal charge (input voltage Vin) that is obtained from the photoelectric converter device 21, to the signal line Lsig by being turned on depending on a row scanning signal to be provided from the readout control line Lread. The transistor 22 is composed of an N-channel type (N-type) FET (Field-Effect Transistor) in this example. However, as an alternative, the transistor 22 may be composed of a P-channel type (P-type) FET and the like.

In this embodiment of the present disclosure, the transistor 22 has a so-called dual-gate structure in which two gates (first gate electrode 120A and second gate electrode 120B) that are arranged in opposition to each other with a semiconductor layer (semiconductor layer 126) interposed between are provided.

Figure 3:
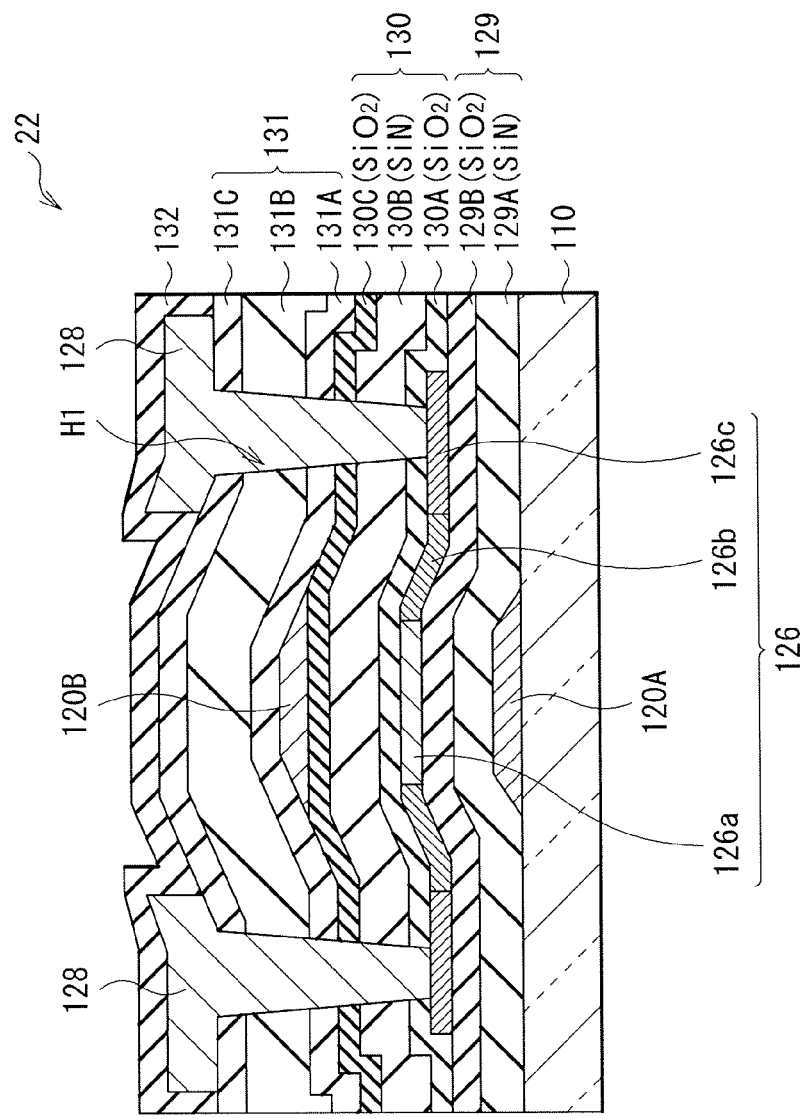
FIG. 3 is a cross-sectional view showing a structure of a transistor illustrated in FIG. 2.

FIG. 3 shows a cross-sectional structure of the transistor 22. The transistor 22 has, on a substrate 110, a first gate electrode 120A (first gate electrode), and a first gate insulating film 129 (first gate insulating film) that is formed so as to cover the first gate electrode 120A. On the first gate insulating film 129, there is provided a semiconductor layer 126 including a channel layer (active layer) 126a, an LDD (Lightly Doped Drain) layer 126b, and an N+ layer 126c. A second gate insulating film 130 (second gate insulating film) is formed so as to cover the semiconductor layer 126, and a second gate electrode 120B (second gate electrode) is provided at a region facing the first gate electrode 120A on the second gate insulating film 130. On the second gate electrode 120B, there is formed a first inter-layer insulating film 131 having contact holes H1, and source-drain electrodes 128 are formed to bury the contact holes H1. On the first inter-layer insulating film 131 and the source-drain electrodes 128, there is provided a second inter-layer insulating film 132.

The semiconductor layer 126 may be composed of, for example, a silicon-based semiconductor such as amorphous silicon, microcrystal silicon, and polycrystal silicon (polysilicon), preferably an LTPS (Low Temperature Polysilicon) material. Alternatively, the semiconductor layer 126 may be also composed of an oxide semiconductor such as indium gallium zinc oxide (InGaZnO) and zinc oxide (ZnO). On the semiconductor layer 126, the LDD layer 126b is formed between the channel layer 126a and the N+ layer 126c to reduce any leakage current. The source-drain electrodes 128, which function as a source or a drain, may be a single-layer film composed of any one of materials such as titanium (Ti), aluminum (Al), molybdenum (Mo), tungsten (W), and chromium (Cr), or a laminated film containing two or more thereof.

Each of the first gate electrode 120A and the second gate electrode 120B may be a single-layer film composed of any one of materials such as molybdenum, titanium, aluminum, tungsten, and chromium, or a laminated film containing two or more thereof. As described above, the first gate electrode 120A and the second gate electrode 120B are provided in opposition to each other with the first gate insulating film 129, the semiconductor layer 126, and the second gate insulating film 130 interposed between.

(Structure of Gate Insulating Film)

Each of the first gate insulating film 129 and the second gate insulating film 130 may be composed to include a silicon oxide film (silicon compound film containing oxygen) such as silicon oxide (SiOx) and silicon oxynitride (SiON). In concrete terms, each of the first gate insulating film 129 and the second gate insulating film 130 may be a single-layer film composed of a material such as silicon oxide and silicon oxynitride, or a laminated film containing such a silicon oxide film and a silicon nitride film such as a silicon nitride (SiNx) film. On each of the first gate insulating film 129 and the second gate insulating film 130, there is provided the above-described silicon oxide film at the semiconductor layer 126 side (next to the semiconductor layer 126). When the semiconductor layer 126 may be composed of, for example, any material as described above (amorphous silicon, microcrystal silicon, polycrystal silicon, and oxide semiconductor), the silicon oxide film is formed next to the semiconductor layer 126 due to a reason for a manufacturing process.

Each of the first gate insulating film 129 and the second gate insulating film 130 may be preferably a laminated film containing the silicon oxide film and the silicon nitride film as described above. In this embodiment of the present disclosure, each of the first gate insulating film 129 and the second gate insulating film 130 is a laminated film. More specifically, the first gate insulating film 129 may have, for example, a silicon nitride film 129A and a silicon oxide film 129B that are laminated in this order from the substrate 110 side. The second gate insulating film 130 may have, for example, a silicon oxide film 130A, a silicon nitride film 130B, and a silicon oxide film 130C that are laminated in this order from the semiconductor layer 126 side. It is to be noted that the silicon oxide film 129B according to this embodiment of the present disclosure corresponds to a specific but not limitative example of a "first silicon oxide film" of the present disclosure, and the silicon oxide film 130A corresponds to a specific but not limitative example of a "second silicon oxide film" of the present disclosure.

In this embodiment of the present disclosure, in the above-described structure, the silicon oxide film 130A of the second gate insulating film 130 that is disposed on the semiconductor layer 126 is smaller in thickness than the silicon oxide film 129B of the first gate insulating film 129 (has a thin-film structure). Further, a total sum in thickness of the silicon oxide films within the second gate insulating film 130 may be, for example, equal to or less than a total sum in thickness of the silicon oxide films within the first gate insulating film 129.

To cite an example of a thickness for each of the first gate insulating film 129 and the second gate insulating film 130, the silicon nitride film 129A may be, for example, within a range of about 50 to 100 nm in thickness, and the silicon oxide film 129B may be, for example, within a range of about 5 to 100 nm in thickness in the first gate insulating film 129. Further, in the second gate insulating film 130, the silicon oxide film 130A may be, for example, within a range of about 5 to 50 nm in thickness, the silicon nitride film 130B may be, for example, within a range of about 50 to 100 nm in thickness, and the silicon oxide film 130C may be, for example, within a range of about 5 to 50 nm in thickness.

Hereupon, a capacitance (referred to as a gate capacitance C1) between the semiconductor layer 126 and the first gate electrode 120A is determined depending on a dielectric constant, a thickness, and the like of each film that composes the first gate insulating film 129. A capacitance (referred to as a gate capacitance C2) between the semiconductor layer 126 and the second gate electrode 120B is determined depending on a dielectric constant, a thickness, and the like of each film that composes the second gate insulating film 130. Meanwhile, as described above, the silicon oxide films 129B and 130A are placed next to the semiconductor layer 126 due to a reason for a manufacturing process, and the silicon oxide films 129B and 130A may be preferably small in thickness from the viewpoint of the transistor characteristics (to be hereinafter detailed). Therefore, for the first gate insulating film 129, in the above-described laminated structure, the gate capacitance C1 is set up by mainly adjusting a thickness of the silicon nitride film 129A. In the second gate insulating film 130, in the above-described laminated structure, the gate capacitance C2 is set up by mainly adjusting a thickness of the silicon nitride film 130B.

For example, when the design is performed to ensure that the gate capacitances C1 and C2 are equivalent to each other in the transistor 22, a thickness of each film is set up as follows. That is, in the first gate insulating film 129, a thickness of each of the silicon nitride film 129A and the silicon oxide film 129B is about 92 nm and about 10 nm, respectively. On the other hand, in the second gate insulating film 130, a thickness of each of the silicon oxide film 130A, the silicon nitride film 130B, and the silicon oxide film 130C is about 5 nm, about 92 nm, and about 5 nm, respectively.

Alternatively, the gate capacitances C1 and C2 may be different from each other in the transistor 22. However, the design may be preferably performed in such a manner that the gate capacitances C1 and C2 are equivalent to each other as described above, or the gate capacitance C2 is greater than the gate capacitance C1. As will hereinafter be described in detail, in the transistor 22, there is a tendency that the transistor characteristics of an upper part thereof (a part corresponding to the semiconductor layer 126, the second gate insulating film 130, and the second gate electrode 120B) may be inferior to those of a lower part thereof (a part corresponding to the semiconductor layer 126, the first gate insulating film 129, and the first gate electrode 120A). Accordingly, to match the characteristics above and below the semiconductor layer 126, the gate capacitance C2 may be preferably greater than the gate capacitance C1. In this case, for example, a thickness of the silicon nitride film 130B may be adjusted to be smaller (for instance, in an example of each thickness as described above, a thickness of the silicon nitride film 130B may be adjusted to be smaller than about 92 nm).

It is to be noted that, in this embodiment of the present disclosure, the first gate electrode 120A of the transistor 22 as described above may be connected with, for example, the readout control line Lread1, while the second gate electrode 120B may be connected with, for example, the readout control line Lread2. This may result in, for example, the same voltage being applied to the first gate electrode 120A and the second gate electrode 120B equally (the same potential is held by performing electrical short-circuiting). However, an electrical control may be carried out separately for the first gate electrode 120A and the second gate electrode 120B, and for example, a pulse voltage may be applied to one of them, while a bias voltage may be applied to the other. A source (source-drain electrode 128) of the transistor 22 may be connected with, for example, the signal line Lsig, while a drain (source-drain electrode 128) may be connected with, for example, a cathode of the photoelectric converter device 21 via the storage node N. Further, an anode of the photoelectric converter device 21 is connected with a ground (grounded).

Each of the first inter-layer insulating film 131 and the second inter-layer insulating film 132 may be a single-layer film that is composed of any one of materials such as silicon oxide, silicon oxynitride, and silicon nitride, or may be a laminated film containing two or more thereof. For example, the first inter-layer insulating film 131 may have a silicon oxide film 131A, a silicon nitride film 131B, and a silicon oxide film 131C that are laminated in this order from the substrate 110 side, and the second inter-layer insulating film 132 may be composed of, for example, a silicon oxide film or a silicon nitride film.

(Row Scanning Section 13)

The row scanning section 13, which is configured to include a shift register circuit, a predetermined logic circuit, and the like to be hereinafter described, is a pixel driving section (row scanning circuit) that carries out a drive (line sequential scanning) on each row basis (on each horizontal line basis) for the plurality of pixels 20 within the pixel section 11. More specifically, an image pickup operation such as a reading operation and a reset operation for each of the pixels 20, may be performed by a line sequential scanning, for example. It is to be noted that such a line sequential scanning is carried out by providing the above-described scan signal to each of the pixels 20 via the readout control line Lread.

Figure 4:
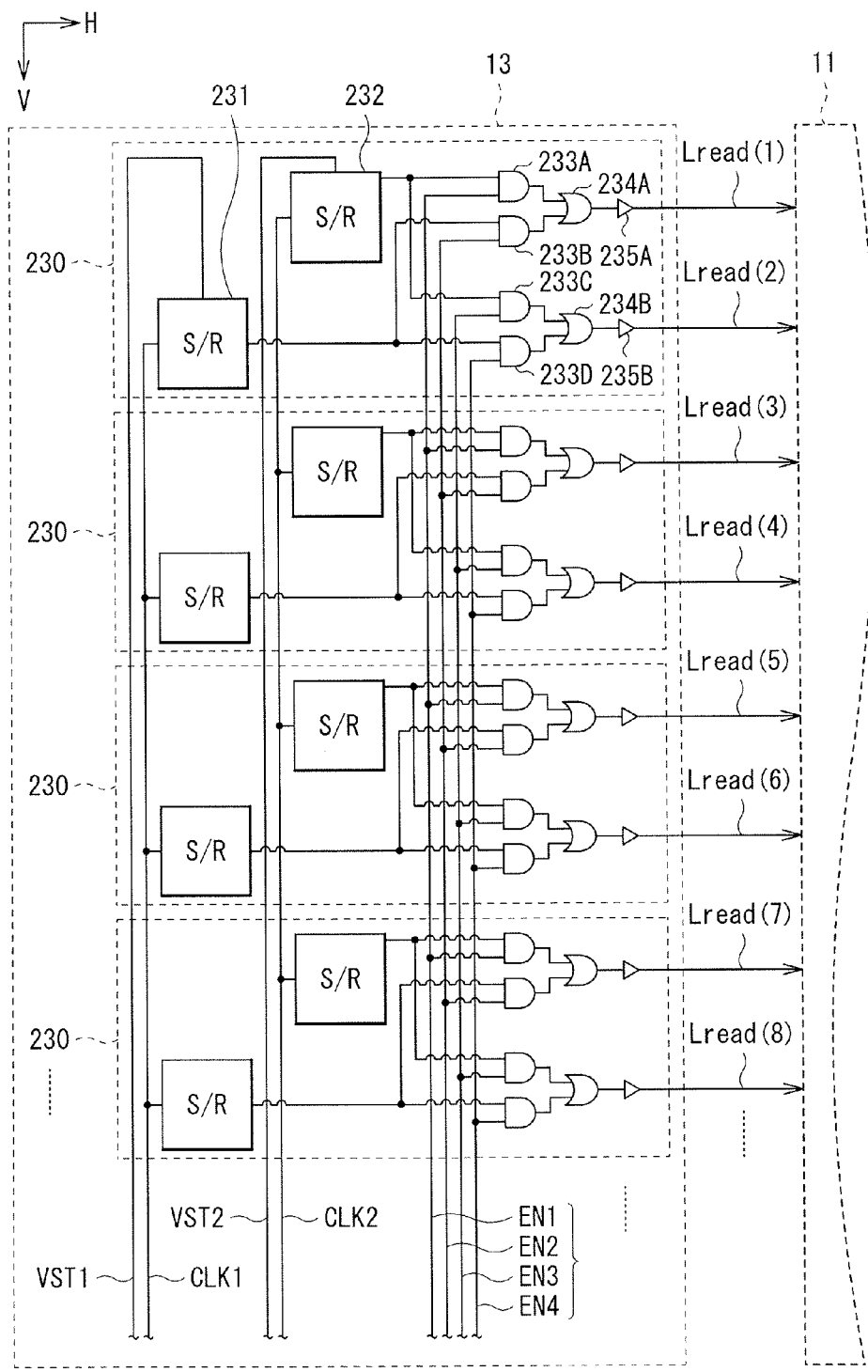
FIG. 4 is a schematic block diagram showing a detailed configuration example of a row scanning section illustrated in FIG. 1.

FIG. 4 shows a block configuration example of the row scanning section 13. The row scanning section 13 has a plurality of unit circuits 230 that extend along the V direction. It is to be noted that eight readout control lines Lread that are connected with four unit circuits 230 shown in FIG. 4 are denoted as Lread (1) to Lread (8) beginning at the top.

Each of the unit circuits 230 may have, for example, shift register circuits 231 and 232 in one or more lines (two lines here) (denoted as "S/R" for the sake of simplicity within a block in the drawing; the same applies hereinafter), four AND circuits (logical multiplication circuits) 233A to 233D, two OR circuits (logical sum circuits) 234A and 234B, and two buffer circuits 235A and 235B. Here, as an example, the description is provided on a configuration having the shift register circuits in two lines, although a configuration having the shift register circuits in a single line may be also permitted. However, a provision of the shift register circuits in two lines or more allows a plurality of times of reset operation to be performed during a single frame period (not described in detail).

The shift register circuit 231 is a circuit to generate pulse signals that are shifted sequentially in the V direction as a whole of the plurality of unit circuits 230 based on a start pulse VST1 and a clock signal CLK1 to be provided from the system control section 16. Similarly, the shift register circuit 232 is a circuit to generate pulse signals that are shifted sequentially in the V direction as a whole of the plurality of unit circuits 230 based on a start pulse VST2 and a clock signal CLK2 to be provided from the system control section 16. Accordingly, for example, the shift register circuit 231 may generate pulse signals for a first-time reset driving, while the shift register circuit 232 may generate pulse signals for a second-time reset driving.

Four types of enable signals EN1 to EN4 for controlling (specifying) a valid period of each pulse signal (each output signal) that is output from the shift register circuits 231 and 232 are input to each of the AND circuits 233A to 233D. In concrete terms, in the AND circuit 233A, a pulse signal from the shift register circuit 232 is input to a first input terminal, while the enable signal EN1 is input to a second input terminal. In the AND circuit 233B, a pulse signal from the shift register circuit 231 is input to a first input terminal, while the enable signal EN2 is input to a second input terminal. In the AND circuit 233C, a pulse signal from the shift register circuit 232 is input to a first input terminal, while the enable signal EN3 is input to a second input terminal. In the AND circuit 233D, a pulse signal from the shift register circuit 231 is input to a first input terminal, while the enable signal EN4 is input to a second input terminal.

The OR circuit 234A is a circuit that generates a logical sum signal (OR signal) of an output signal from the AND circuit 233A and an output signal from the AND circuit 233B. Similarly, the OR circuit 234B is a circuit that generates a logical sum signal of an output signal from the AND circuit 233C and an output signal from the AND circuit 233D. In such a manner, through an operation in conjunction with the above-described AND circuits 233A to 233D, as well as the OR circuits 234A and 234B, a logical sum signal of output signals (pulse signals) from the shift register circuits 231 and 232 is generated while controlling a valid period of each output signal. As a result, this may specify a drive timing and the like in performing a plurality of times of a reset driving, for example.

The buffer circuit 235A is a circuit that functions as a buffer for an output signal (pulse signal) from the OR circuit 234A, while the buffer circuit 235B is a circuit that functions as a buffer for an output signal from the OR circuit 234B. Pulse signals (row scan signals) that are buffered by the buffer circuits 235A and 235B are then output to each of the pixels 20 within the pixel section 11 via the readout control line Lread.

(A/D Conversion Section 14)

The A/D conversion section 14, which has a plurality of column selection sections 17 that are provided one-by-one for each plurality of signal lines Lsig (four lines in this example), performs A/D conversion (analog-to-digital conversion) based on a signal voltage (voltage corresponding to a signal charge) that is input via the signal line Lsig. Through such an operation, an output data Dout (image pickup signal) in a digital signal is generated to be output externally.

Figure 5:
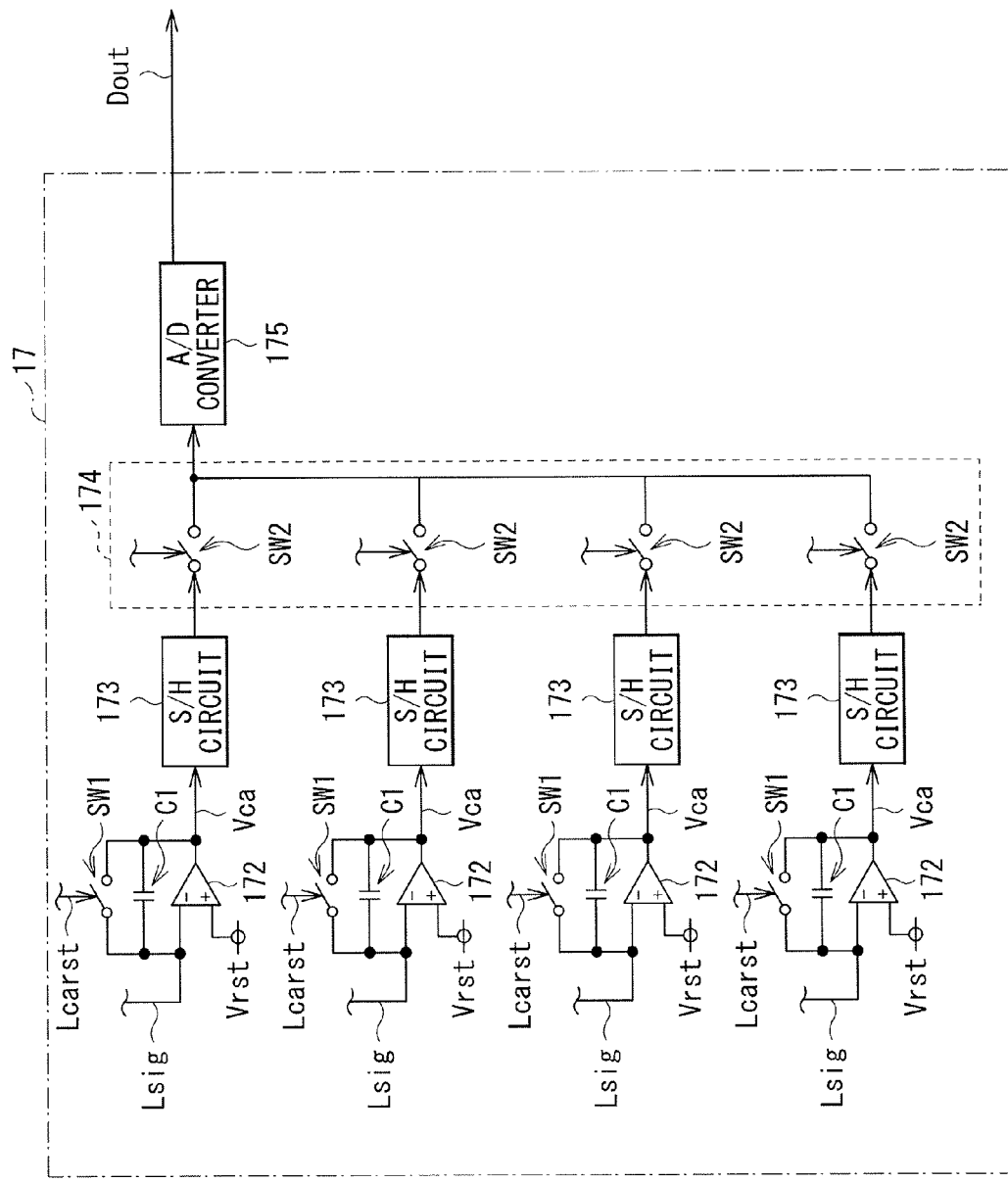
FIG. 5 is a schematic block diagram showing a detailed configuration example of a column selection section illustrated in FIG. 1.

As shown in FIG. 5, for example, each of the column selection sections 17 may have charge amplifiers 172, capacitor devices (capacitors, feedback capacitor devices, or the like) C1, switches SW1, sample/hold (S/H) circuits 173, a multiplexer circuit (selection circuit) 174 including four switches SW2, and an A/D converter 175. Among those, the charge amplifier 172, the capacitor device C1, the switch SW1, the S/H circuit 173, and the switch SW2 are provided for each of the signal lines Lsig. The multiplexer circuit 174 and the A/D converter 175 are provided for each of the column selection sections 17.

The charge amplifier 172 is an amplifier for converting a signal charge that is read out from the signal line Lsig into a voltage (Q-V conversion). In the charge amplifier 172, one end of the signal line Lsig is connected with a negative-side (minus-side) input terminal, and a predetermined reset voltage Vrst is input to a positive-side (plus-side) input terminal. Between an output terminal and the negative-side input terminal of the charge amplifier 172, a return connection (feedback connection) is performed via a parallel connecting circuit of the capacitor device C1 and the switch SW1. In other words, a first terminal of the capacitor device C1 is connected with the negative-side input terminal of the charge amplifier 172, while a second terminal thereof is connected with the output terminal of the charge amplifier 172. Similarly, a first terminal of the switch SW1 is connected with the negative-side input terminal of the charge amplifier 172, while a second terminal thereof is connected with the output terminal of the charge amplifier 172. It is to be noted that an on/off state of the switch SW1 is controlled with a control signal (amplifier reset control signal) that is provided via an amplifier reset control line Lcarst from the system control section 16.

The S/H circuit 173, which is disposed between the charge amplifier 172 and the multiplexer circuit 174 (switches SW2), is a circuit for temporarily holding an output voltage Vca from the charge amplifier 172.

The multiplexer circuit 174 is a circuit to make a connection or shut off a connection selectively between each of the S/H circuits 173 and the A/D converter 175 in such a manner that one of the four switches SW2 turns on sequentially according to a scan driving which is performed by the column scanning section 15.

The A/D converter 175 is a circuit to generate and output the above-described output data Dout by performing A/D conversion on an output voltage from the S/H circuit 173 that is input via the switch SW2.

(Column Scanning Section 15)

The column scanning section 15, which may be configured to include a shift register, an address decoder, and the like that are not shown in the drawing, drives sequentially while scanning each of the switches SW2 within the above-described column selection section 17. Through such a selective scanning that is performed by the column scanning section 15, a signal (above-described output data Dout) for each of the pixels 20 that is read out via each of the signal lines Lsig is sequentially output externally.

(System Control Section 16)

The system control section 16 controls each operation of the row scanning section 13, the A/D conversion section 14, and the column scanning section 15. More specifically, the system control section 16 has a timing generator that generates various timing signals (control signals) as described previously, and carries out a drive control for the row scanning section 13, the A/D conversion section 14, the column scanning section 15, and a bias voltage correcting section 18 based on various timing signals that are generated in the timing generator. Based on a control by the system control section 16, each of the row scanning section 13, the A/D conversion section 14, and the column scanning section 15 performs an image pickup driving (line sequential image pickup driving) for the plurality of pixels 20 within the pixel section 11, thereby obtaining the output data Dout from the pixel section 11.

(Function and Advantageous Effects)

In the image pickup unit 1 according to this embodiment of the present disclosure, for example, when a radiation ray or radiation-based light enters the pixel section 11, an incident light-based signal charge is generated (photoelectric conversion is performed) in each of the pixels 20 (photoelectric converter devices 21 in this case). On this occasion, more specifically, in the storage node N, a voltage variation occurs corresponding to a node capacitance due to storage of signal charges that are generated by the photoelectric conversion. In response to such a voltage variation, an input voltage Vin (voltage corresponding to a signal charge) is provided to a drain of the transistor 22. Thereafter, when the transistor 22 turns on depending on a row scanning signal provided from the readout control line Lread, the above-described signal charge is read out onto the signal line Lsig.

The signal charges that are read out in such a manner are output to the column selection section 17 within the A/D conversion section 14 for each plurality of pixel columns (four pixel columns in this case) via the signal line Lsig. In the column selection section 17, to begin with, Q-V conversion (conversion from a signal charge into a signal voltage) is carried out in the charge amplifier circuit that is composed of the charge amplifier 172, and the like for each of the signal charges input from each signal line Lsig. Subsequently, A/D conversion is performed in the A/D converter 175 via the S/H circuit 173 and the multiplexer circuit 174 for each of the converted signal voltages (output voltages Vca from the charge amplifier 172) to generate the output data Dout (image pickup signal) in a digital signal. In such a manner, the output data Dout is output sequentially from each of the column selection sections 17 to be transmitted externally (or to be input to an internal memory that is not shown in the drawing).

Hereupon, some radiation rays (X-rays) entering the image pickup unit 1 may leak into the pixel section 11 without being subject to wavelength conversion, and if the transistor 22 is exposed to such a radiation ray, the following defect may occur. Specifically, the transistor 22 has oxygen-containing films (silicon oxide films 129B and 130A) on the first gate insulating film 129 and the second gate insulating film 130. If a radiation ray enters such an oxygen-containing film, electrons in the film may be excited due to a so-called photoelectric effect, Compton scattering, electron-pair creation, or the like. As a result, holes may be trapped to build up within the first gate insulating film 129 and the second gate insulating film 130, and holes may be also trapped to build up at an interface between the channel layer 126a and the silicon oxide film 129B and an interface between the channel layer 126a and the silicon oxide film 130A. This may cause the characteristics of the transistor 22 to deteriorate. For example, this may result in a shift in a threshold voltage Vth, deterioration in the S (threshold) value, or the like, which could become contributing factors to cause increased off current, decreased on current, or the like.

Consequently, in this embodiment of the present disclosure, the silicon oxide film 130A on the second gate insulating film 130 is made smaller in thickness than the silicon oxide film 129B on the first gate insulating film 129. This makes it possible to effectively suppress any deterioration in the transistor characteristics as described above. Hereinafter, the description is provided on the reason.

Figure 6A:
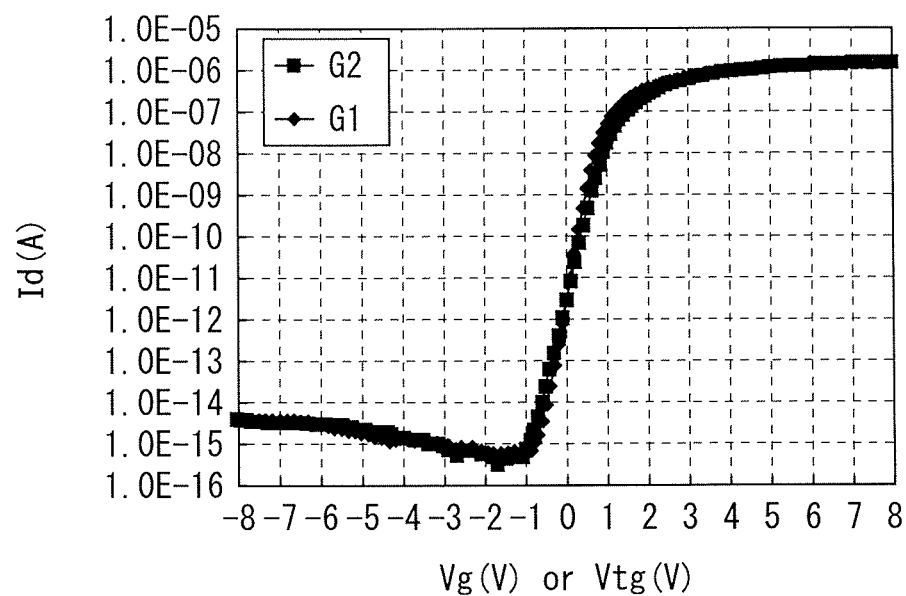
FIG. 6A is a characteristic diagram for explaining the effect of each gate voltage to be applied to two top and bottom gate electrodes on current and voltage characteristics.
Figure 6B:
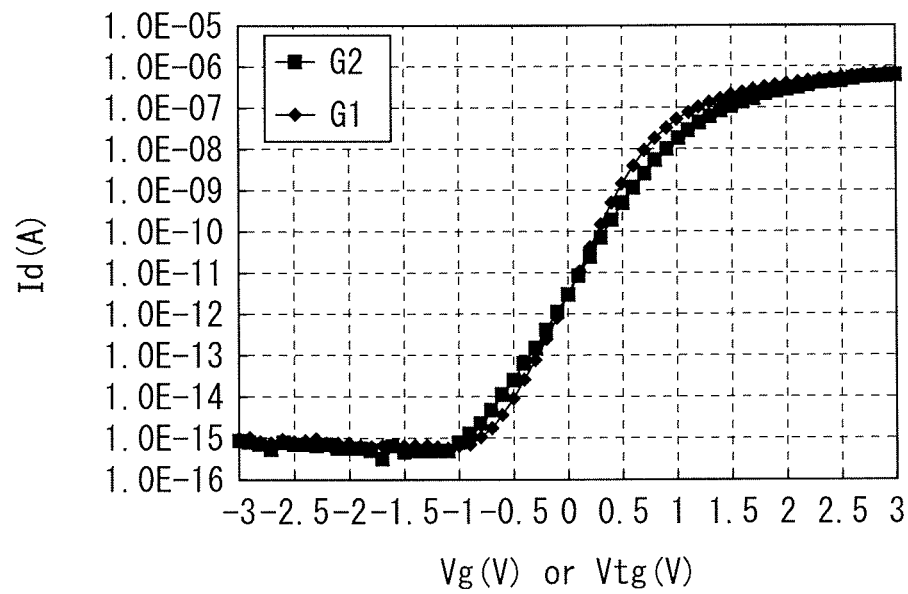
FIG. 6B is a characteristic diagram showing, in an enlarged manner, a part of a range of the gate voltage in the characteristic diagram illustrated in FIG. 6A.

Each of FIG. 6A and FIG. 6B shows a relationship of a drain current (current between source and drain) Id versus a gate voltage Vg or Vtg of the transistor 22. It is to be noted that the gate voltage Vg is a voltage to be applied to the first gate electrode 120A, while the gate voltage Vtg is a voltage to be applied to the second gate electrode 120B. FIG. 6A shows each of a relationship between the gate voltage Vg and the drain current Id (characteristics G1) and a relationship between the gate voltage Vtg and the drain current Id (characteristics G2). However, the gate voltage Vg is varied with the gate voltage Vtg fixed to 0 V (ground) during a measurement of the characteristics G1, while the gate voltage Vtg is varied with the gate voltage Vg fixed to 0 V (ground) during a measurement of the characteristics G2. FIG. 6B shows a part of a range in FIG. 6A, in an enlarged manner.

Figure 7:
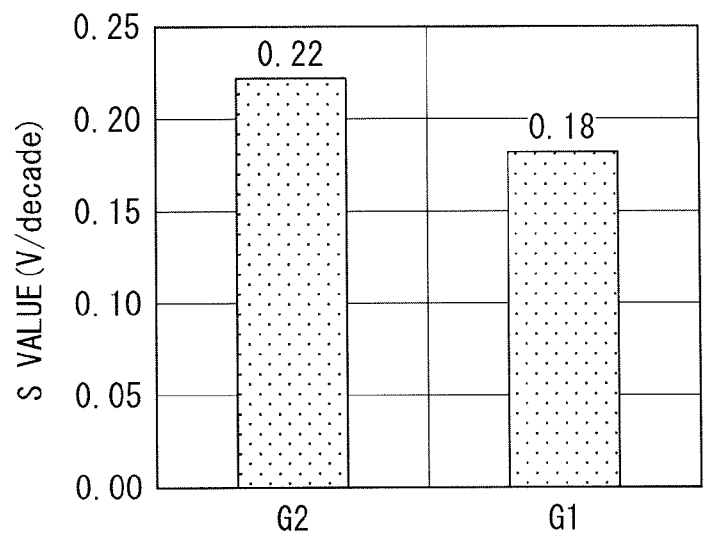
FIG. 7 is a characteristic diagram for explaining the effect of each gate voltage to be applied to two top and bottom gate electrodes on an S (threshold) value.

FIG. 7 shows the S value in each of the above-described characteristics G1 and G2.

As seen from the drawing, the characteristics G2 when the gate voltage Vtg is varied are inferior to the characteristics G1 when the gate voltage Vg is varied (worse than the characteristics G1). In concrete terms, as shown in FIG. 6A (FIG. 6B) and FIG. 7, it is found that the S value when the gate voltage Vtg is varied is worse than the S value when the gate voltage Vg is varied. Further, a threshold voltage is also shifted. This is due to the following reason. That is, in a manufacturing process, in forming the first gate insulating film 129, the semiconductor layer 126, and the second gate insulating film 130, the silicon nitride film 129A, the silicon oxide film 129B, the semiconductor layer 126, the silicon oxide film 130A, the silicon nitride film 130B, and the silicon oxide film 130C are formed in this order on the substrate 110. Among those, the silicon nitride film 129A, the silicon oxide film 129B, and the semiconductor layer 126 are formed continuously in a vacuum chamber, and thereafter the substrate 110 is once taken out of the chamber (exposed to the atmospheric air) due to a reason for a manufacturing process. For example, when a low temperature polycrystal silicon material is used for the semiconductor layer 126, in carrying out a crystallization (ELA: Excimer Laser Anneal) process, the substrate 110 is once taken out of the chamber. As a result, a state of an interface between the silicon oxide film 129B and the semiconductor layer 126 becomes favorable (it is less likely that contamination and the like will occur), but it is more likely that a state of an interface between the semiconductor layer 126 and the silicon oxide film 130A will deteriorate (it is more likely that contamination and the like will occur).

As described above, in the transistor 22, a state of an interface at the upside of the semiconductor layer 126 (interface between the semiconductor layer 126 and the silicon oxide film 130A) is inferior to an interface at the downside (interface between the semiconductor layer 126 and the silicon oxide film 129B), and thus it is likely that deterioration in characteristics that may be caused by trapped holes as described above will occur. Consequently, as mentioned previously, the silicon oxide film 130A on the second gate insulating film 130 is made smaller in thickness than the silicon oxide film 129B on the first gate insulating film 129, thereby allowing to alleviate the effect of such a state of an interface and to suppress any deterioration in characteristics. In particular, when a drive is carried out with the first gate electrode 120A and the second gate electrode 120B short-circuited (with these gate electrodes held at the same potential), the characteristics of any part at the upside of the semiconductor layer 126 become dominant in the transistor 22, and thus it is possible to effectively suppress any deterioration in the transistor characteristics by reducing a thickness of the silicon oxide film 130A.

Further, the second gate insulating film 130 is configured as the laminated film as described above, thereby allowing to set the gate capacitance C2 at a desired value in a manner of, for example, adjusting a thickness of the silicon nitride film 130B. Hereupon, in the transistor 22, since it is likely that the characteristics of any part at the upside of the semiconductor layer 126 will deteriorate due to a reason for a manufacturing process, a setup may be preferably made to ensure that the gate capacitance C2 is greater than the gate capacitance C1. The second gate insulating film 130 is configured as the laminated film as described above, and a thickness of the silicon nitride film 130B is adjusted to be smaller, thereby allowing to set the gate capacitances C1 and C2 having a magnitude relation as such.

As described above, in this embodiment of the present disclosure, in the transistor 22 for reading out a radiation-based signal charge from each of the pixels 20, the first gate electrode 120A, the first gate insulating film 129, the semiconductor layer 126, the second gate insulating film 130, and the second gate electrode 120B are provided in this order, wherein the first gate insulating film 129 includes the silicon oxide film 129B at the semiconductor layer 126 side and the second gate insulating film 130 includes the silicon oxide film 130A at the semiconductor layer 126 side. Here, in the course of a manufacturing process, it is likely that a state of an interface between the semiconductor layer 126 and the second gate insulating film 130 (that is, silicon oxide film 130A) will deteriorate, which may cause deterioration in the characteristics of the transistor 22. The silicon oxide film 130A is smaller in thickness than the silicon oxide film 129B, and thus it is possible to alleviate the effect of such a deteriorated state of an interface. As a result, this allows to suppress any deterioration in the transistor characteristics and to achieve high reliability.

Figure 8:
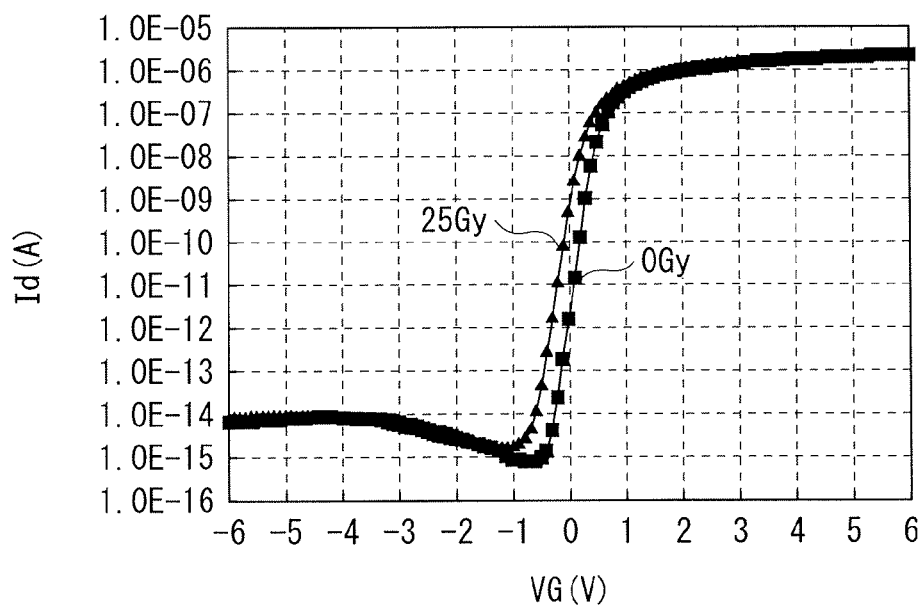
FIG. 8 is a diagram showing current and voltage characteristics before and after irradiation of an X-ray to a transistor according to an example 1.

FIG. 8 shows the current and voltage characteristics of an example 1 (each case of pre-irradiation (cumulative dose: 0 Gy) and post-irradiation (25 Gy) of an X-ray to the transistor 22 having a laminated configuration illustrated in FIG. 1). As seen from the drawing, in this embodiment of the present disclosure, it is possible to suppress any deterioration in the characteristics (shift in a threshold voltage, deterioration in the S value, and the like) that may be caused by irradiation of an X-ray. It is to be noted that, in an example in FIG. 8, each of the first gate electrode 120A and the second gate electrode 120B has a width of about 2.0 micrometers and a length of about 2.5 micrometers, and an LDD layer is formed on the semiconductor layer 126. Further, a source-drain voltage Vds is about 0.1 V, and the first gate electrode 120A and the second gate electrode 120B are short-circuited to be held at the same potential (gate voltage VG (=Vg=Vtg)). A value of the gate voltage VG is varied within a range of about −6 to +6 V.

Subsequently, the description is provided on modification examples according to the above-described embodiment of the present disclosure. It is to be noted that any component parts essentially same as those in the above-described embodiment are denoted with the same reference numerals, and the related description is omitted as appropriate.

Modification Example 1

Figure 9:
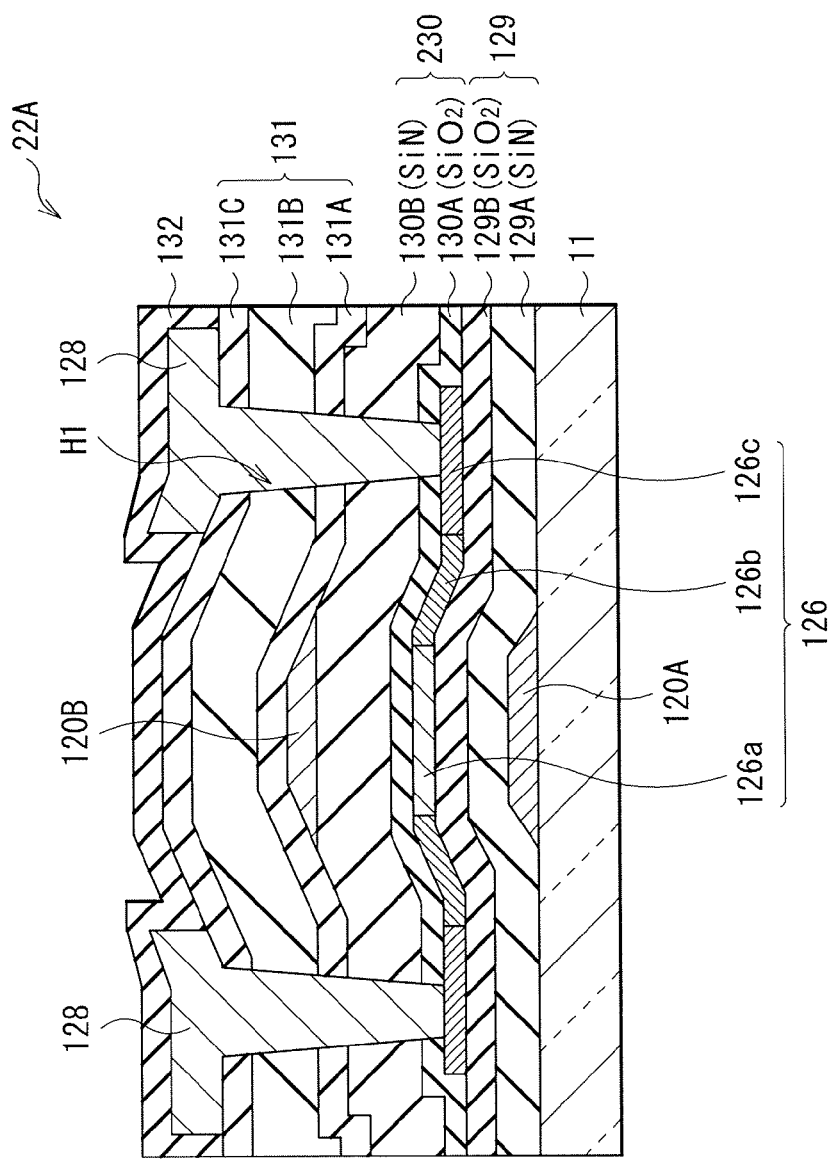
FIG. 9 is a cross-sectional view showing a structure of a transistor according to a modification example 1.

FIG. 9 shows a cross-sectional structure of a transistor (transistor 22A) according to a modification example 1. In the above-described embodiment of the present disclosure (example in FIG. 3), the second gate insulating film (second gate insulating film 130) is a three-layer laminated film in which the silicon oxide film 130A, the silicon nitride film 130B, and the silicon oxide film 130C are stacked in this order from the semiconductor layer 126 side, although a laminated structure of the second gate insulating film is not limited thereto. For example, like a second gate insulating film (second gate insulating film 230) on the transistor 22A according to the modification example 1, a two-layer structure may be permitted in which the silicon oxide film 130A and the silicon nitride film 130B are stacked in this order from the semiconductor layer 126 side. When the silicon oxide film 130A that is formed next to the semiconductor layer 126 is smaller in thickness than the silicon oxide film 129B, it is possible to obtain the advantageous effects equivalent to those in the above-described embodiment of the present disclosure.

Figure 10A:
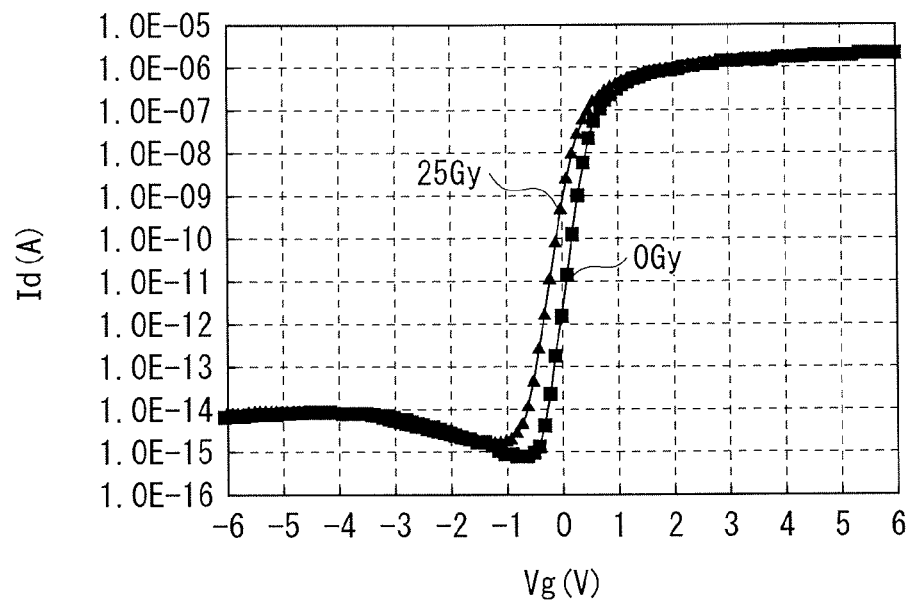
FIG. 10A is a diagram showing the current and voltage characteristics before and after irradiation of an X-ray to the transistor according to the example 1.
Figure 10B:
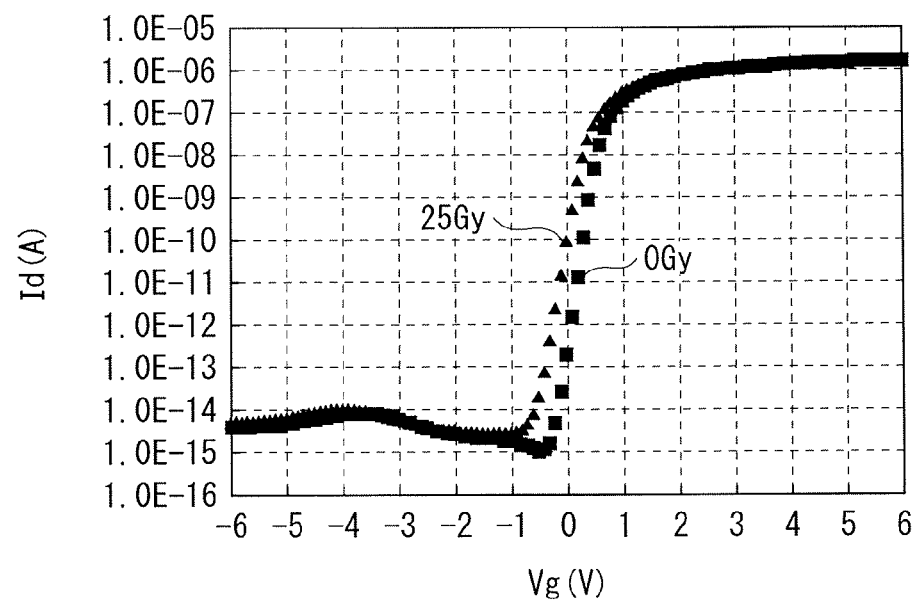
FIG. 10B is a diagram showing the current and voltage characteristics before and after irradiation of an X-ray to the transistor illustrated in FIG. 9.
Figure 11:
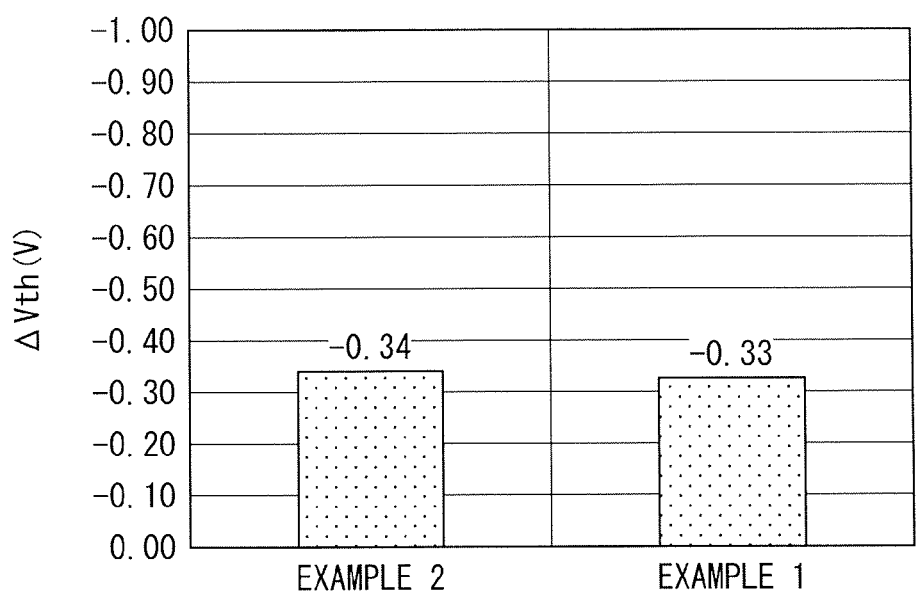
FIG. 11 is a characteristic diagram showing an amount of shift in a threshold voltage in each case of examples 1 and 2.

FIG. 10A shows the current and voltage characteristics of the above-described example 1 (same as those illustrated in FIG. 8), and FIG. 10B shows the current and voltage characteristics of the transistor 22A according to the modification example 1 (example 2). It is to be noted that measurement conditions in FIG. 10B are the same as those in a case with FIG. 8. Further, FIG. 11 shows the amount of shift in the threshold voltage Vth (d (delta) Vth) after irradiation of the X-ray 25 Gy in the current and voltage characteristics for each of the examples 1 and 2. It is to be noted that the threshold voltage Vth is based on a case where the current Id is about $1.0*10^{-13}$ (A). FIG. 10B and FIG. 11 indicate that, also in the transistor 22A according to the modification example 1, it is less likely that deterioration in the characteristics will occur, as with the transistor 22 according to the above-described embodiment of the present disclosure. In other words, the silicon oxide film 130C that is not adjacent to the semiconductor layer 126 is considered to have a less influence on the transistor characteristics. This also indicates that making the silicon oxide film 130A that is adjacent to the semiconductor layer 126 among the second gate insulating film 230 smaller in thickness effectively suppresses deterioration in characteristics.

Modification Example 2

Figure 12:
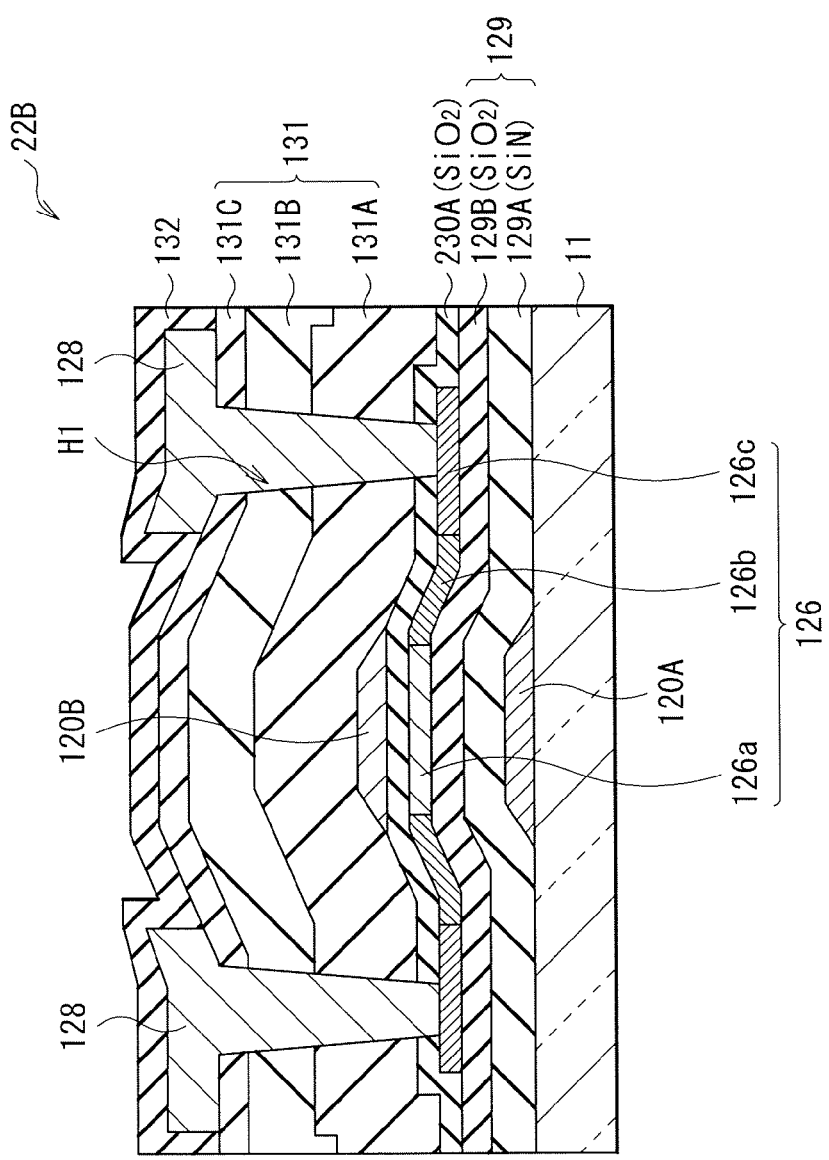
FIG. 12 is a cross-sectional view showing a structure of a transistor according to a modification example 2.

FIG. 12 shows a cross-sectional structure of a transistor (transistor 22B) according to a modification example 2. In the above-described modification example 1, the second gate insulating film is configured in a two-layer structure, although like the modification example 2, a second gate insulating film 230A that is configured of a single-layer film of a silicon oxide film may be provided on the semiconductor layer 126. Even though the second gate insulating film 230A is configured of a single-layer film of a silicon oxide film in such a manner, it is possible to obtain the advantageous effects equivalent to those in the above-described embodiment of the present disclosure.

Further, the gate capacitance C2 is increased by virtue of a single-layer structure, which facilitates to perform a control for making the gate capacitance C2 larger than the gate capacitance C1.

Modification Example 3

Figure 13:
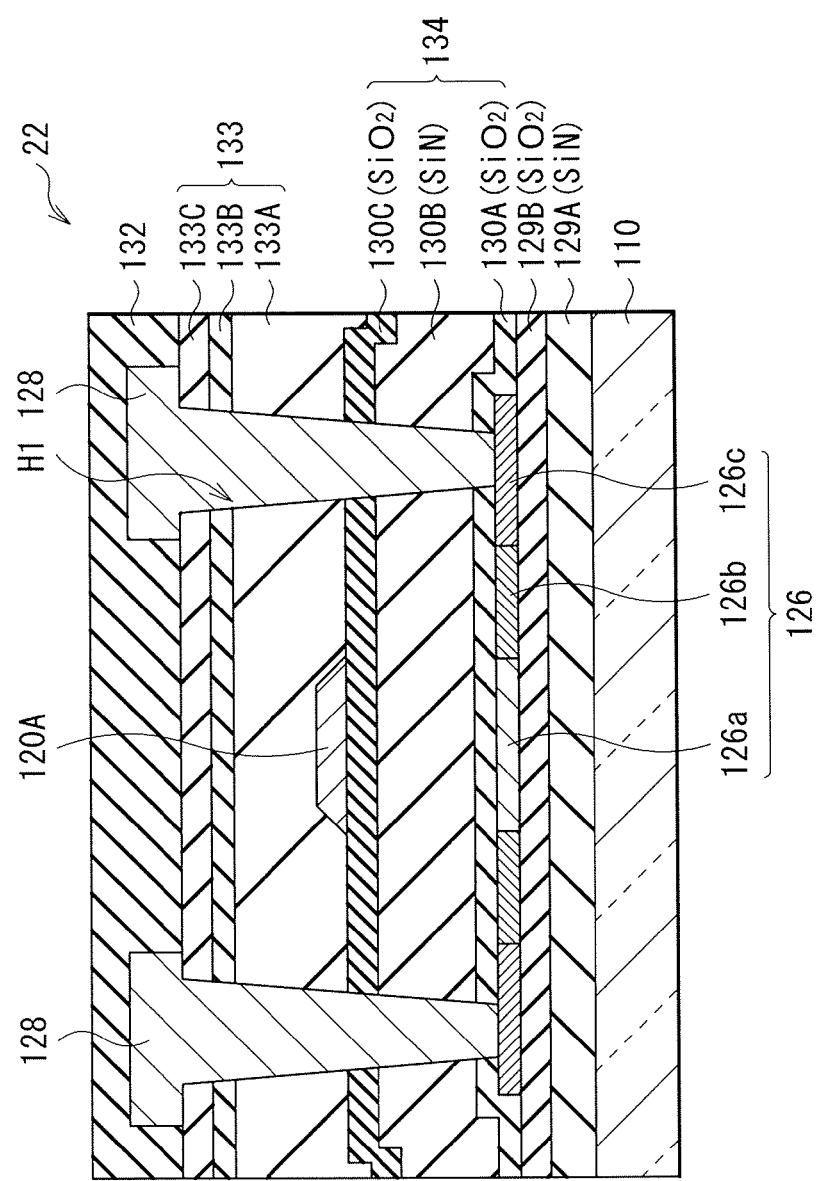
FIG. 13 is a cross-sectional view showing a structure of a transistor according to a modification example 3.

FIG. 13 shows a cross-sectional structure of a transistor according to a modification example 3. In the above-described embodiment of the present disclosure, a device structure of a dual-gate type is exemplified, although a transistor according to the embodiment of the present disclosure may be configured in a device structure of a top-gate type as found in the modification example 3. A device structure according to the modification example 3 may have, for example, a silicon nitride film 129A, a silicon oxide film 129B, a semiconductor layer 126, a first gate insulating film 134, and a first gate electrode 120A in this order from the substrate 110 side. The first gate insulating film 134 may have the same laminated structure as that in the second gate insulating film 130 according to the above-described embodiment of the present disclosure, for example. Further, on the first gate insulating film 134 and the first gate electrode 120A, a first inter-layer insulating film 133 is formed, and contact holes H1 are formed that run through the first inter-layer insulating film 133 and the first gate insulating film 134. On the first inter-layer insulating film 133, there is provided source-drain electrodes 128 to bury the contact holes H1. The first inter-layer insulating film 133 is a laminated film that may have, for example, a silicon oxide film 133A, a silicon nitride film 133B, and a silicon oxide film 133C in this order from the first gate electrode 120A side. A second inter-layer insulating film 132 is provided so as to cover the first inter-layer insulating film 133 and the source-drain electrodes 128.

Also in the modification example 3, the silicon oxide film 130A has the thickness smaller than that of the silicon oxide film 129B, which makes it possible to obtain the advantageous effects equivalent to those of the above-described embodiment of the present disclosure.

It is to be noted that, also in the modification example 3, a laminated structure of the first gate insulating film 134 is not limited to the above-described one, but either a two-layer structure or a single-layer film of a silicon oxide material may be permitted provided that a silicon oxide film is included.

Modification Example 4

Figure 14:
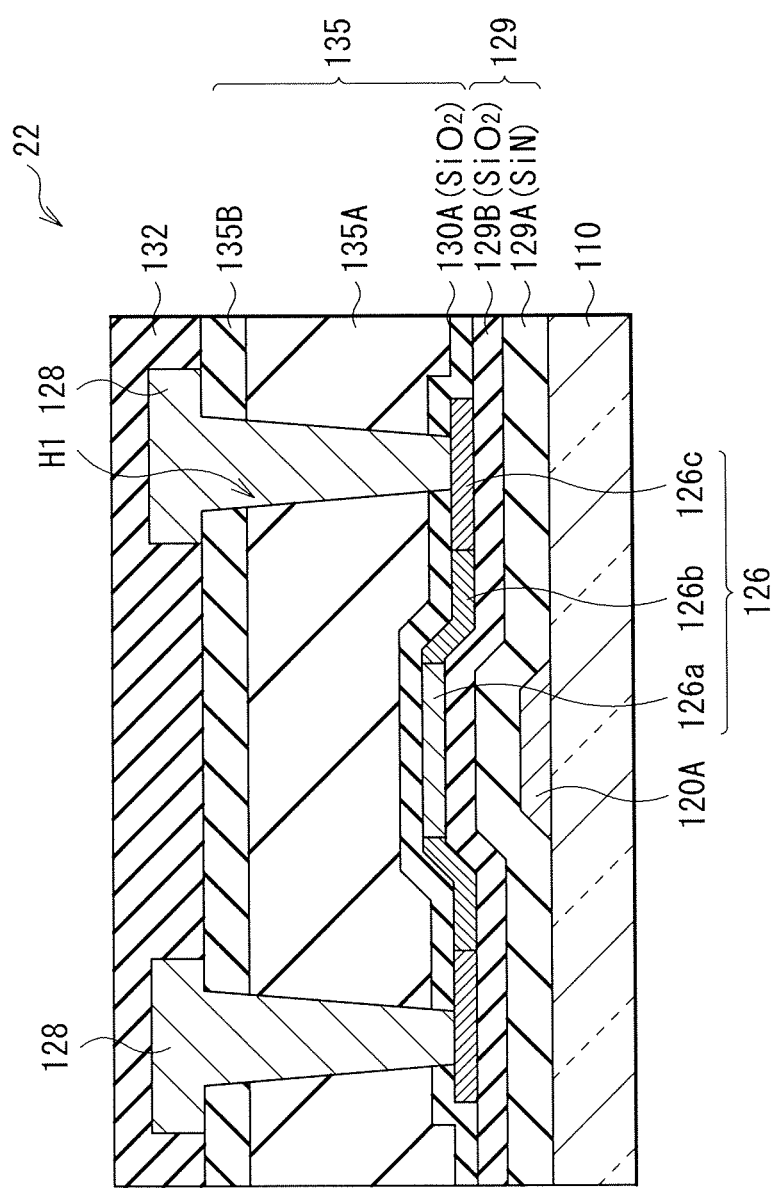
FIG. 14 is a cross-sectional view showing a structure of a transistor according to a modification example 4.

FIG. 14 shows a cross-sectional structure of a transistor according to a modification example 4. In the above-described embodiment of the present disclosure, a device structure of a dual-gate type is exemplified, although a transistor according to the embodiment of the present disclosure may be configured in a device structure of a bottom-gate type as found in the modification example 4. A device structure according to the modification example 4 may have, for example, a first gate electrode 120A, a first gate insulating film 129, a semiconductor layer 126, and a silicon oxide film 130A in this order from the substrate 110 side. Further, on the silicon oxide film 130A, for example, a silicon nitride film 135A and a silicon oxide film 135B may be laminated, and the silicon oxide film 130A, the silicon nitride film 135A, and the silicon oxide film 135B configure a first inter-layer insulating film 135. Contact holes H1 are formed that run through the first inter-layer insulating film 135. On the first inter-layer insulating film 135, there is provided source-drain electrodes 128 to bury the contact holes H1.

Also in the modification example 4, the silicon oxide film 130A has the thickness smaller than that of the silicon oxide film 129B, which makes it possible to obtain the advantageous effects equivalent to those of the above-described embodiment of the present disclosure.

Modification Example 5

Figure 15:
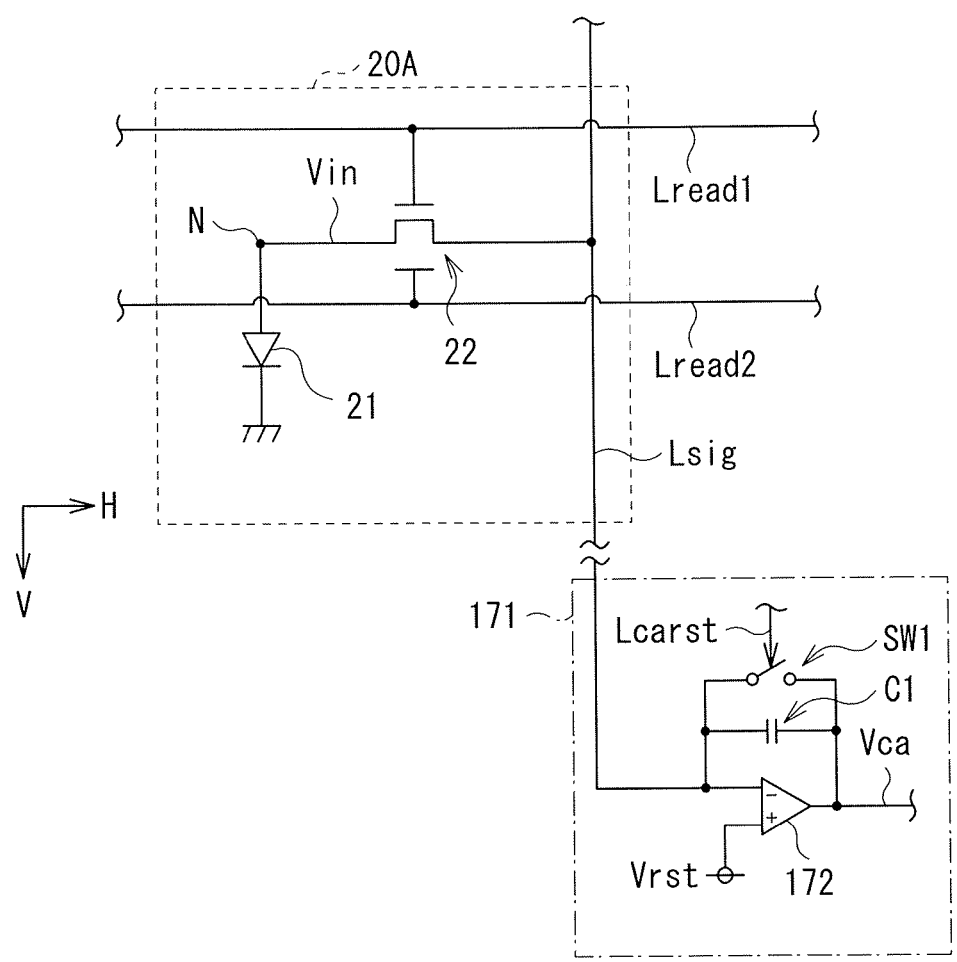
FIG. 15 is a circuit diagram showing a configuration of a pixel and the like according to a modification example 5.

FIG. 15 shows a circuit configuration of a pixel (pixel 20A) according to a modification example 5 along with a circuit configuration example of the charge amplifier circuit 171 that is described in the above-described embodiment of the present disclosure. The pixel 20A according to the modification example 5, which adopts a circuit configuration of a so-called passive type as with the pixel 20 according to the above-described embodiment of the present disclosure, has one photoelectric converter device 21 and one transistor 22. Further, readout control lines Lread (Lread1 and Lread2) that extend along the H direction and a signal line Lsig that extends along the V direction are connected with the pixel 20A.

In the pixel 20A according to the modification example 5, however, unlike the pixel 20 according to the above-described embodiment of the present disclosure, an anode of the photoelectric converter device 21 is connected with a storage node N, and a cathode thereof is connected with a ground (grounded). In such a manner, in the pixel 20A, the storage node N may be connected with the anode of the photoelectric converter device 21, and even though such a configuration is made, it is possible to obtain the advantageous effects equivalent to those of the above-described embodiment of the present disclosure.

Modification Example 6

Figure 16:
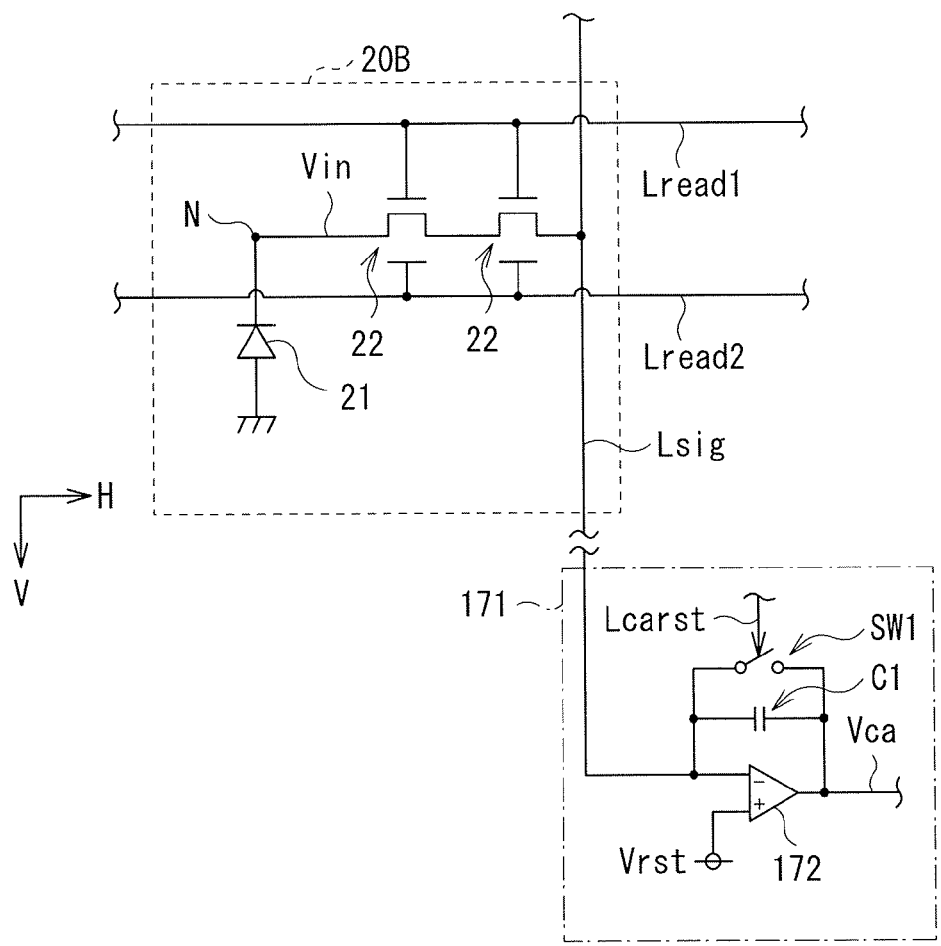
FIG. 16 is a circuit diagram showing a configuration of a pixel and the like according to a modification example 6.

FIG. 16 shows a circuit configuration of a pixel (pixel 20B) according to a modification example 6 along with a circuit configuration example of the charge amplifier circuit 171 that is described in the above-described embodiment of the present disclosure. The pixel 20B according to the modification example 6, which has a circuit configuration of a so-called passive type as with the pixel 20 according to the above-described embodiment of the present disclosure, has one photoelectric converter device 21, and is connected with readout control lines Lread1 and Lread2 that extend along the H direction and a signal line Lsig that extends along the V direction.

In the modification example 6, however, the pixel 20B has two transistors 22. These two transistors 22 are connected in series with each other (a source or a drain of one transistor is electrically connected with a source or a drain of the other transistor, respectively). Further, one gate on each of the transistors 22 is connected with the readout control line Lread1, while the other gate is connected with the readout control line Lread2. It is possible to reduce any off-leakage current by providing two transistors 22 in a single pixel 20B in such a manner.

As described above, two transistors 22 that are connected in series with each other may be provided within the pixel 20B, and even in such a case, it is possible to obtain the advantageous effects equivalent to those of the above-described embodiment of the present disclosure. It is to be noted that three or more transistors may be connected in series with one another.

Modification Examples 7-1 and 7-2

Figure 17:
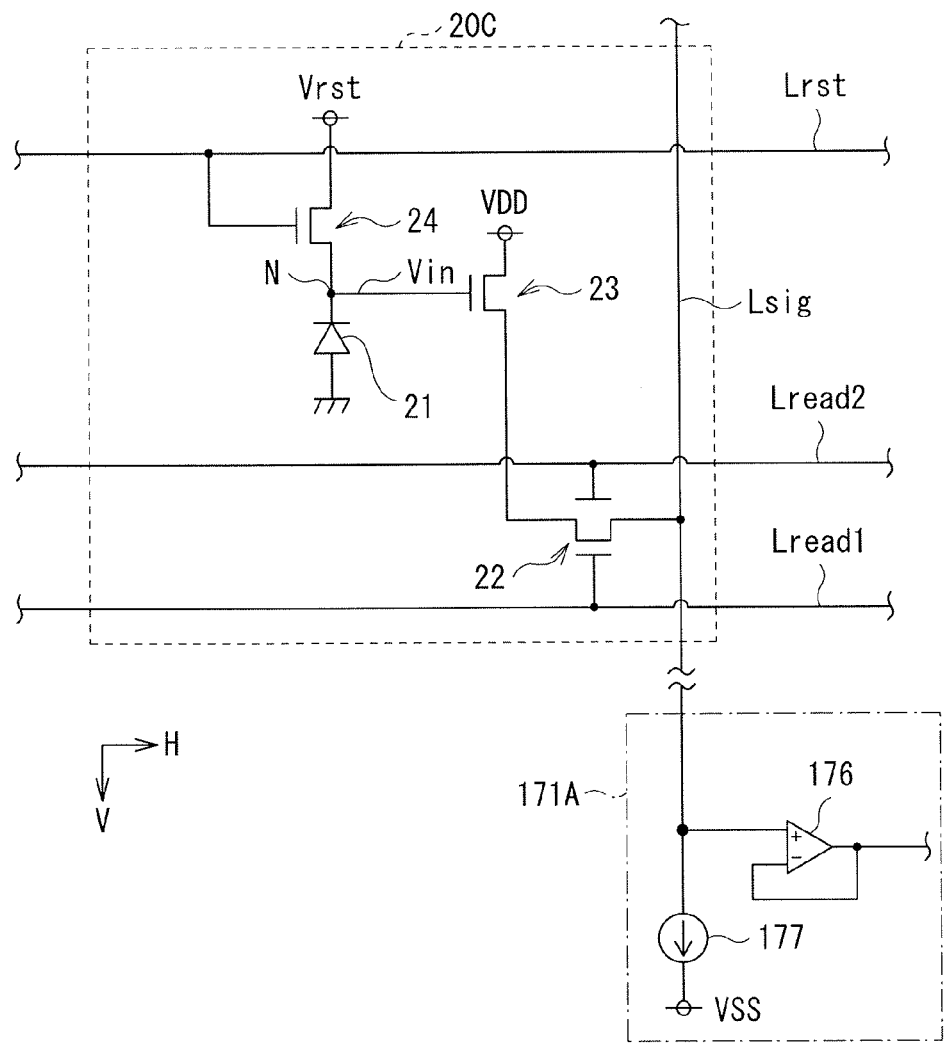
FIG. 17 is a circuit diagram showing a configuration of a pixel and the like according to a modification example 7-1.
Figure 18:
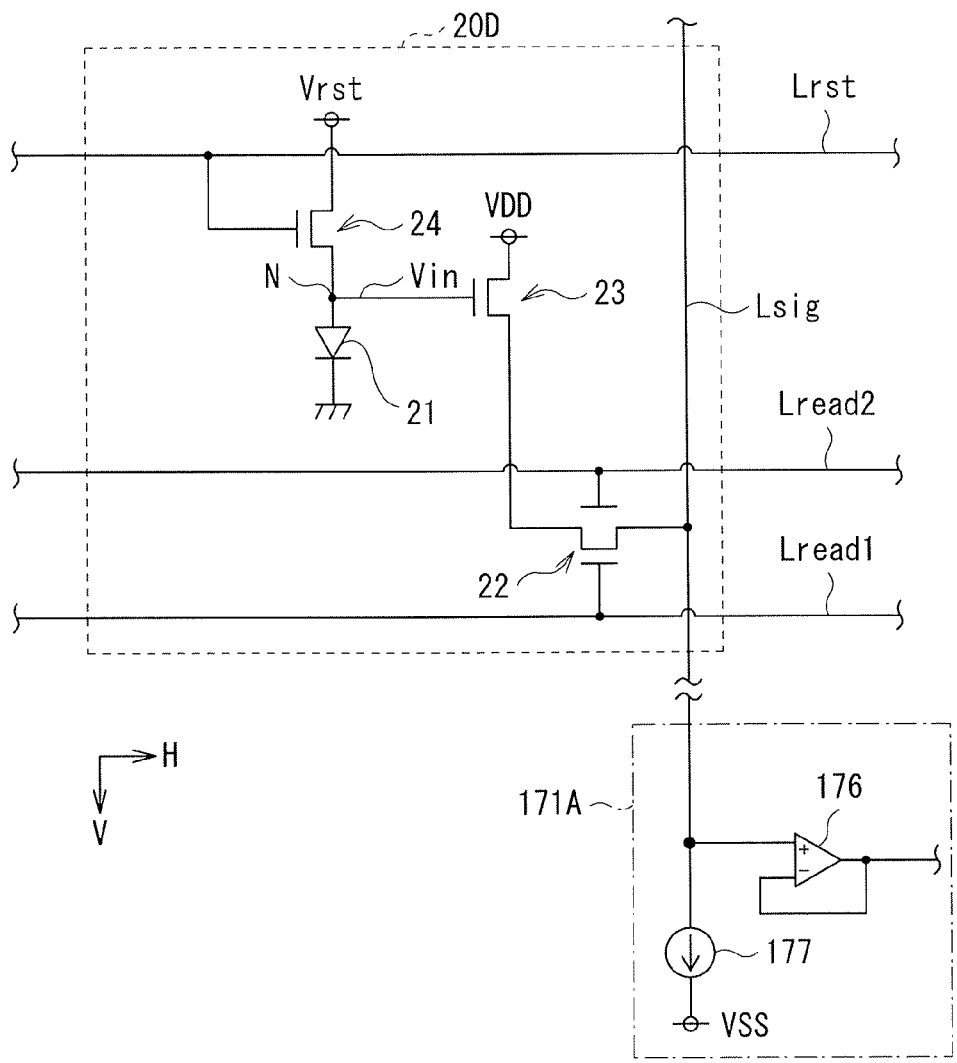
FIG. 18 is a circuit diagram showing a configuration of a pixel and the like according to a modification example 7-2.

FIG. 17 shows a circuit configuration of a pixel (pixel 20C) according to a modification example 7-1 along with a circuit configuration example of a charge amplifier circuit 171A that is described below. Further, FIG. 18 shows a circuit configuration of a pixel (pixel 20D) according to a modification example 7-2 along with a circuit configuration example of the charge amplifier circuit 171A. Unlike the pixels 20, 20A, and 20B that are described thus far, each of the pixels 20C and 20D according to these modification examples 7-1 and 7-2 has a pixel circuit of a so-called active type.

Each of the pixels 20C and 20D of an active type is provided with one photoelectric converter device 21 as well as three transistors 22, 23, and 24. Further, readout control lines Lread (Lread1 and Lread2) and a reset control line Lrst that extend along the H direction, and a signal line Lsig that extends along the V direction are connected with each of the pixels 20C and 20D.

In each of the pixels 20C and 20D, a gate of the transistor 22 is connected with the readout control line Lread, a source thereof is connected with the signal line Lsig, and a drain thereof is connected with a drain of the transistor 23 that configures a source-follower circuit. A source of the transistor 23 is connected with a power supply VDD, and a gate thereof is connected with a cathode (example in FIG. 17) or an anode (example in FIG. 18) of the photoelectric converter device 21 and a drain of the transistor 24 that functions as a reset transistor via the storage node N. A gate of the transistor 24 is connected with the reset control line Lrst, and a reset voltage Vrst is applied to a source thereof. An anode of the photoelectric converter device 21 is connected with a ground in the modification example 7-1, while a cathode of the photoelectric converter device 21 is connected with a ground in the modification example 7-2.

Further, in these modification examples 7-1 and 7-2, the charge amplifier circuit 171A is provided with an amplifier 176 and a constant current source 177 instead of the charge amplifier 172, the capacitor device C1, and the switch SW1 in the above-descried charge amplifier circuit 171. In the amplifier 176, the signal line Lsig is connected with a positive-side input terminal, and a negative-side input terminal and an output terminal are connected with each other to form a voltage-follower circuit. It is to be noted that a first terminal of the constant current source 177 is connected with one end side of the signal line Lsig, while the power supply VDD is connected with a second terminal of the constant current source 177.

Modification Examples 8-1 and 8-2

Figure 19A:
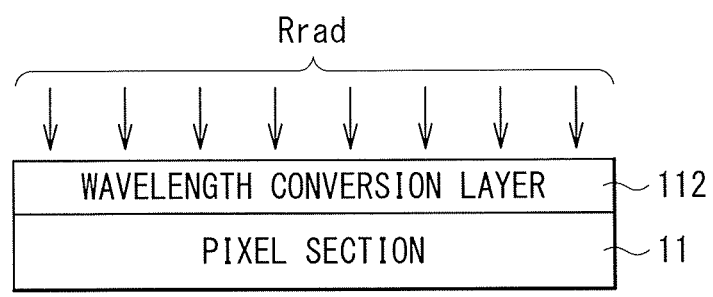
FIG. 19A is a schematic diagram for explaining an image pickup unit according to a modification example 8-1.
Figure 19B:
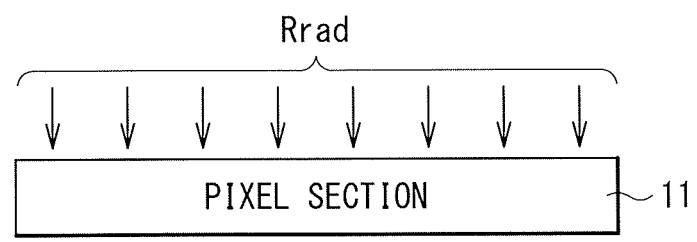
FIG. 19B is a schematic diagram for explaining an image pickup unit according to a modification example 8-2.

Each of FIG. 19A and FIG. 19B schematically shows a simplified configuration of a pixel section 11 according to each of modification examples 8-1 and 8-2. When the image pickup unit 1 according to the above-described embodiment of the present disclosure is a radiographic image pickup unit, the pixel section 11 has a configuration in either the modification example 8-1 or 8-2.

The pixel section 11 according to the modification example 8-1 that is illustrated in FIG. 19A, which is applicable to a so-called indirect-conversion type radiographic image pickup unit, has a wavelength conversion layer 112 thereon (at a light-receiving surface side). The wavelength conversion layer 112 converts a wavelength of a radiation ray Rrad (alpha ray, beta ray, gamma ray, X-ray, and the like) into a wavelength within a sensitivity zone of the photoelectric converter device 21 in the pixel section 11, and this allows information based on the radiation ray Rrad to be read out in the pixel section 11. The wavelength conversion layer 112 may be composed of, for example, a fluorescent material (for instance, scintillator) that converts a radiation ray such as an X-ray into visible light. This wavelength conversion layer 112 may be configured by laminating, for example, an organic planarizing film or a planarizing film composed of a spin-on glass material and the like, and a fluorescent material film. The fluorescent material film may be composed of, for example, CsI (with the addition of Tl), $Gd_2O_2S$, BaFX (X is Cl, Br, I, and the like), NaI, $CaF_2$, or the like.

The pixel section 11 according to the modification example 8-2 that is illustrated in FIG. 19B, which is applicable to a so-called direct-conversion type radiographic image pickup unit, has a function that absorbs an incident radiation ray Rrad to convert it into an electric signal. The pixel section 11 according to the modification example 8-2 may be composed of, for example, an amorphous selenium (a-Se) semiconductor, a cadmium telluride (CdTe) semiconductor, and the like. It is to be noted that a circuit configuration of the pixel 20 in the case of this direct-conversion type is equivalent to a circuit configuration where the photoelectric converter device 21 is replaced with a capacitor in each of the component parts illustrated in FIG. 2.

The indirect-conversion type or direct-conversion type radiographic image pickup unit as described above is utilized as a various type of image pickup unit that obtains an electric signal based on a radiation ray Rrad. Such a radiographic image pickup unit may be applicable to, for example, an X-ray image pickup unit (digital radiography, and the like) for medical application, an X-ray image pickup unit for a carried personal belongings inspection in use at an airport or any other facilities, an industrial X-ray image pickup unit (for example, a unit for inspection of dangerous objects inside a container), and the like.

(Application Example)

Further, the image pickup units according to the above-described embodiment and modification examples of the present disclosure are also applicable to an image pickup display system as mentioned hereinafter.

Figure 20:
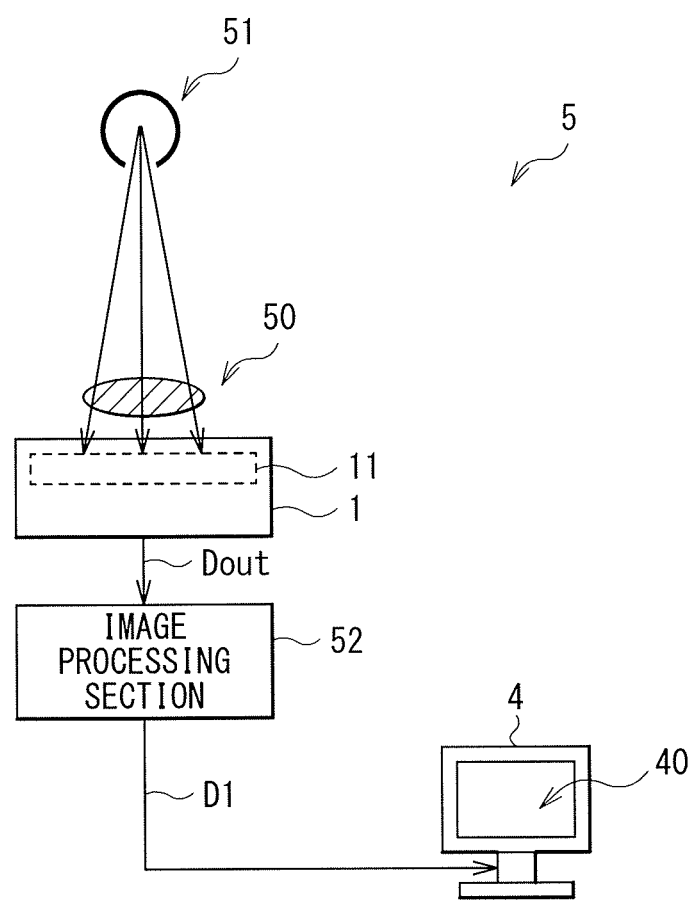
FIG. 20 is a schematic diagram showing a simplified configuration of an image pickup display system according to an application example.

FIG. 20 schematically shows a simplified configuration example of an image pickup display system (image pickup display system 5) according to an application example. The image pickup display system 5, which includes the image pickup unit 1 having the pixel section 11 and other component parts according to the above-described embodiment and the like of the present disclosure, an image processing section 52, and a display unit 4, is an image pickup display system using a radiation ray (radiographic image pickup display system) in this example.

The image processing section 52 generates image data D1 by performing a predetermined image processing operation on output data Dout (image pickup signal) that is output from the image pickup unit 1. The display unit 4 carries out an image display based on the image data D1 that is generated by the image processing section 52 on a predetermined monitor screen 40.

In the image pickup display system 5, the image pickup unit 1 (radiographic image pickup unit in this example) acquires image data Dout of an object 50 based on irradiated light (radiation ray in this example) that is irradiated from a light source (radiation source such as X-ray source in this example) toward the object 50 to output such image data Dout to the image processing section 52. The image processing section 52 performs the above-described predetermined image processing operation on the incoming image data Dout to output the image data (display data) D1 on which the image processing has been performed to the display unit 4. The display unit 4 displays image information (imaged picture) on the monitor screen 40 based on the incoming image data D1.

As described above, in the image pickup display system 5 according to this application example, it is possible to acquire an image of the object 50 as an electrical signal in the image pickup unit 1, which allows to perform an image display by transmitting an acquired electrical signal to the display unit 4. In other words, it is possible to view an image of the object 50 without using any radiographic film as found in an existing method, as well as to deal with a motion-image shooting and a motion-image display.

It is to be noted that, in this application example, the description is provided by taking as an example a case where the image pickup unit 1 is configured as a radiographic image pickup unit, and is used as an image pickup display system using a radiation ray, although the image pickup display system according to this embodiment of the present disclosure is applicable to any system using an image pickup unit employing any other method.

The present disclosure is described thus far with reference to the embodiment, the modification examples thereof, and the application example thereof, although the present disclosure is not limited to the above-described embodiment and the like, but different variations are available. For example, in the above-described embodiment and the like, a case where each of the first and second gate insulating films is configured in a laminated structure in which one to three insulating films are stacked is exemplified, although each of the first and second gate insulating films may be configured in a laminated structure in which four or more insulating films are stacked. Even though any laminated structure is adopted, it is possible to obtain the advantageous effects of the present disclosure provided that a silicon oxide film is provided at the semiconductor layer side on the second gate insulating film, and this silicon oxide film is smaller in thickness than a silicon oxide film on the first gate insulating film.

Further, pixel circuit configurations in the pixel section according to the above-described embodiment and the like are not limited to those described in the above-described embodiment and the like (circuit configurations of the pixels 20, and 20A to 20D), but any other circuit configurations may be permitted alternatively. Similarly, circuit configurations of the row scanning section, the column selection section, and the like are also not limited to those described in the above-described embodiment and the like, but any other circuit configurations may be permitted alternatively.

Moreover, each of the pixel section, the row scanning section, the A/D conversion section (column selection section), the column scanning section, and the like that are described in the above-described embodiment and the like may be formed on a same substrate, for example. More specifically, it may be also possible to form switches and the like in these circuit sections on the same substrate by using, for example, a polycrystal semiconductor such as a low temperature polycrystalline silicon. As a result, this may make it possible to carry out a drive operation on the same substrate based on, for example, a control signal from an external system control section, which allows to achieve a narrowed frame structure (three-side free frame structure) and improved reliability at the time of wiring connection.

It is to be noted that the present disclosure may be configured as follows.

(1) A semiconductor device comprising: a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer.

(2) The semiconductor device of (2), wherein the at least one gate electrode comprises a first gate electrode and a second gate electrode, wherein the first gate electrode is nearer to the substrate than the second gate electrode.

(3) The semiconductor device of (2), wherein the semiconductor device is a laminated structure wherein the substrate, the first gate electrode, the first silicon oxide layer, the semiconductor layer, the second insulating layer, and the second gate electrode are arranged in this order.

(4) The semiconductor device of (2), wherein a first portion of the first silicon oxide layer is in physical contact with the semiconductor layer and a second portion of the first silicon oxide layer is in physical contact with the second silicon oxide layer.

(5) The semiconductor device of (2), wherein the semiconductor layer is disposed between the first gate electrode and the second gate electrode.

(6) The semiconductor device of (5), wherein a first capacitance between the first gate electrode and the semiconductor layer is less than or equal to a second capacitance between the second gate electrode and the semiconductor layer.

(7) The semiconductor device of (1), wherein the at least one gate electrode comprises only a first gate electrode.

(8) The semiconductor device of (7), wherein the second silicon oxide layer is nearer to the substrate than the first gate electrode.

(9) The semiconductor device of (8), wherein the semiconductor device is a laminated structure wherein the substrate, the first silicon oxide layer, the semiconductor layer, the second insulating layer, and the first gate electrode are arranged in this order.

(10) The semiconductor device of (7), wherein the first gate electrode is nearer to the substrate than the first silicon oxide layer.

(11) The semiconductor device of claim 10), wherein the semiconductor device is a laminated structure wherein the substrate, the first gate electrode, the first silicon oxide layer, the semiconductor layer, and the second insulating layer, are arranged in this order.

(12) The semiconductor device of (1), wherein the first silicon oxide layer is a portion of a first insulating layer, the first insulating layer comprising a first silicon nitride layer.

(13) The semiconductor device of (12), wherein the second silicon oxide layer is a portion of a second insulating layer, the second insulating layer comprising a second silicon nitride layer.

(14) The semiconductor device of (1), wherein the second silicon oxide layer is a portion of an insulating layer, the insulating layer comprising a silicon nitride layer.

(15) The semiconductor device of claim 1, wherein the semiconductor layer comprises a low temperature polysilicon material.

(16) The semiconductor device of (1), wherein the semiconductor layer comprises microcrystal silicon.

(17) The semiconductor device of (1), wherein the at least one gate electrode comprises at least one material selected from the group consisting of molybdenum, titanium, aluminum, tungsten, and chromium.

(18) An image pick-up device comprising: a plurality of pixels, each pixel comprising at least one semiconductor device, the semiconductor device comprising: a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer.

(19) The image pick-up device of (18), wherein the at least one gate electrode comprises a first gate electrode and a second gate electrode, wherein the first gate electrode is nearer to the substrate than the second gate electrode.

(20) A radiation imaging apparatus comprising: a radiation source configured to emit radiation; and an image pick-up device configured to receive and detect at least a portion of the emitted radiation, the image pick-up device comprising a plurality of pixels, each pixel comprising at least one semiconductor device, the semiconductor device comprising: a substrate; at least one gate electrode; at least two silicon oxide layers comprising a first silicon oxide layer and a second silicon oxide layer, wherein the first silicon oxide layer is nearer to the substrate than the second silicon oxide layer, and wherein a thickness of the first silicon oxide layer is greater than or equal to a thickness of the second silicon oxide layer; and a semiconductor layer disposed between at least a portion of the first silicon oxide layer and at least a portion of the second silicon oxide layer.

Moreover, it is to be noted that the present disclosure may be configured as follows.

(A)

An image pickup unit, including:

a plurality of pixels configured to generate radiation-based signal charges; and a field-effect transistor configured to read out the signal charges from the plurality of pixels, the transistor having a first silicon oxide film, a semiconductor layer including an active layer, and a second silicon oxide film that are laminated in order from a substrate side, and having a first gate electrode arranged in opposition to the semiconductor layer with the first or second silicon oxide film interposed between, wherein the second silicon oxide film is smaller in thickness than the first silicon oxide film.

(B)

The image pickup unit according to (A), wherein the transistor has the first gate electrode, a first gate insulating film including the first silicon oxide film, the semiconductor layer, a second gate insulating film including the second silicon oxide film, and a second gate electrode in this order on the substrate.

(C)

The image pickup unit according to (B), wherein the first gate insulating film or the second gate insulating film or both are laminated films including a silicon nitride film.

(D)

The image pickup unit according to (C), wherein the second gate insulating film is a laminated film including the second silicon oxide film and the silicon nitride film.

(E)

The image pickup unit according to (D), wherein the second gate insulating film includes the second silicon oxide film, the silicon nitride film, and a third silicon oxide film in order from the semiconductor layer side.

(F)

The image pickup unit according to (D), wherein the second gate insulating film is configured by laminating the second silicon oxide film and the silicon nitride film in order from the semiconductor layer side.

(G)

The image pickup unit according to (B) or (C), wherein the second gate insulating film is configured of the second silicon oxide film.

(H)

The image pickup unit according to any one of (B) to (G), wherein a capacitance between the second gate electrode and the semiconductor layer is set up to be equal to or greater than a capacitance between the first gate electrode and the semiconductor layer.

(I)

The image pickup unit according to any one of (B) to (H), further including an inter-layer insulating film including a silicon oxide film on the second gate insulating film.

(J)

The image pickup unit according to (A), wherein the transistor has the first silicon oxide film, the semiconductor layer, the second silicon oxide film, and the first gate electrode in order from the substrate side.

(K)

The image pickup unit according to (A), wherein the transistor has the first gate electrode, the first silicon oxide film, the semiconductor layer, and the second silicon oxide film in order from the substrate side.

(L)

The image pickup unit according to any one of (A) to (K), wherein the semiconductor layer includes polycrystalline silicon, microcrystalline silicon, amorphous silicon, or oxide semiconductor.

(M)

The image pickup unit according to any one of (A) to (L), wherein the semiconductor layer includes low temperature polycrystalline silicon.

(N)

The image pickup unit according to any one of (A) to (M), wherein each of the plurality of pixels has a photoelectric converter device, and a wavelength conversion layer converting a wavelength of the radiation into a wavelength in a sensitivity zone of the photoelectric converter device is provided at a light-incident side on each of the plurality of pixels.

(O)

The image pickup unit according to (N), wherein the photoelectric converter device is composed of a PIN-type photodiode or an MIS-type sensor.

(P)

The image pickup unit according to any one of (A) to (M), wherein each of the plurality of pixels absorbs the radiation to generate the signal charges.

(Q)

The image pickup unit according to any one of (A) to (P), wherein the radiation is an X-ray.

(R)

An image pickup display system provided with an image pickup unit and a display unit configured to perform an image display based on image pickup signals obtained by the image pickup unit, the image pickup unit including: a plurality of pixels configured to generate radiation-based signal charges; and a field-effect transistor configured to read out the signal charges from the plurality of pixels, the transistor having a first silicon oxide film, a semiconductor layer including an active layer, and a second silicon oxide film that are laminated in order from a substrate side, and having a first gate electrode arranged in opposition to the semiconductor layer with the first or second silicon oxide film interposed between, wherein the second silicon oxide film is smaller in thickness than the first silicon oxide film.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 Image pickup unit
11 Pixel section
13 Row scanning section
230 Unit circuit
231, 232 Shift resistor circuit (S/R)
235A, 235B Buffer circuit
233A to 233D AND circuit
234A, 234B OR circuit
14 A/D conversion section
15 Column scanning section
16 System control section
17 Column selection section
171, 171A Charge amplifier circuit
172 Charge amplifier
173 S/H circuit
174 Multiplexer circuit
175 A/D converter
176 Amplifier
177 Constant current source
20, 20A to 20C Pixel (image pickup pixel)
21 Photoelectric converter device
22, 23, 24 Transistor
110 Substrate
120A First gate electrode
120B Second gate electrode
129 First gate insulating film
129A, 130B Silicon nitride film
129B, 130A, 130C Silicon oxide film
126 Semiconductor layer
130, 230, 230A Second gate insulating film
131 First inter-layer insulating film
132 Second inter-layer insulating film
112 Wavelength conversion layer
4 Display unit
40 Monitor screen
5 Image pickup display system
50 Object
51 Light source (radiation source)
52 Image processing section
Lsig Signal line
Lread, Lread1, Lread2 Readout control line
Lrst Reset control line
Lcarst Amplifier reset control line
Dout Output data
N Storage node
SW1 Switch
C1, C2 gate capacitance
Rrad Radiation ray

The invention claimed is:
1. A semiconductor device, comprising:
a substrate;
at least one gate electrode;
at least two silicon oxide layers that comprise a first silicon oxide layer and a second silicon oxide layer, wherein the first silicon oxide layer is nearer to the substrate than the second silicon oxide layer, and wherein a thickness of the first silicon oxide layer is greater than a thickness of the second silicon oxide layer; and
a semiconductor layer disposed between at least a portion of the first silicon oxide layer and at least a portion of the second silicon oxide layer.

2. The semiconductor device of claim 1, wherein the at least one gate electrode comprises a first gate electrode and a second gate electrode, wherein the first gate electrode is nearer to the substrate than the second gate electrode.

3. The semiconductor device of claim 2, wherein the semiconductor device is a laminated structure, wherein the substrate, the first gate electrode, the first silicon oxide layer, the semiconductor layer, a second insulating layer, and the second gate electrode are arranged in this order.

4. The semiconductor device of claim 2, wherein a first portion of the first silicon oxide layer is in physical contact with the semiconductor layer and a second portion of the first silicon oxide layer is in physical contact with the second silicon oxide layer.

5. The semiconductor device of claim 2, wherein the semiconductor layer is disposed between the first gate electrode and the second gate electrode.

6. The semiconductor device of claim 5, wherein a first capacitance between the first gate electrode and the semiconductor layer is less than or equal to a second capacitance between the second gate electrode and the semiconductor layer.

7. The semiconductor device of claim 1, wherein the at least one gate electrode comprises only a first gate electrode.

8. The semiconductor device of claim 7, wherein the second silicon oxide layer is nearer to the substrate than the first gate electrode.

9. The semiconductor device of claim 8, wherein the semiconductor device is a laminated structure, wherein the substrate, the first silicon oxide layer, the semiconductor layer, a second insulating layer, and the first gate electrode are arranged in this order.

10. The semiconductor device of claim 7, wherein the first gate electrode is nearer to the substrate than the first silicon oxide layer.

11. The semiconductor device of claim 10, wherein the semiconductor device is a laminated structure, wherein the substrate, the first gate electrode, the first silicon oxide layer, the semiconductor layer, and a second insulating layer, are arranged in this order.

12. The semiconductor device of claim 1, wherein the first silicon oxide layer is a portion of a first insulating layer, wherein the first insulating layer comprises a first silicon nitride layer.

13. The semiconductor device of claim 12, wherein the second silicon oxide layer is a portion of a second insulating layer, wherein the second insulating layer comprises a second silicon nitride layer.

14. The semiconductor device of claim 1, wherein the second silicon oxide layer is a portion of an insulating layer, wherein the insulating layer comprises a silicon nitride layer.

15. The semiconductor device of claim 1, wherein the semiconductor layer comprises a low temperature polysilicon material.

16. The semiconductor device of claim 1, wherein the semiconductor layer comprises microcrystal silicon.

17. The semiconductor device of claim 1, wherein the at least one gate electrode comprises at least one material selected from the group consisting of molybdenum, titanium, aluminum, tungsten, and chromium.

18. An image pick-up device, comprising:
a plurality of pixels, wherein each pixel of the plurality of pixels comprises at least one semiconductor device, wherein the semiconductor device comprises:

a substrate;

at least one gate electrode;

at least two silicon oxide layers that comprises a first silicon oxide layer and a second silicon oxide layer, wherein the first silicon oxide layer is nearer to the substrate than the second silicon oxide layer, and wherein a thickness of the first silicon oxide layer is greater than a thickness of the second silicon oxide layer; and a semiconductor layer disposed between at least a portion of the first silicon oxide layer and at least a portion of the second silicon oxide layer.

19. The image pick-up device of claim 18, wherein the at least one gate electrode comprises a first gate electrode and a second gate electrode, wherein the first gate electrode is nearer to the substrate than the second gate electrode.

20. A radiation imaging apparatus, comprising:

a radiation source configured to emit radiation; and an image pick-up device configured to receive and detect at least a portion of the emitted radiation, wherein the image pick-up device comprises a plurality of pixels, wherein each pixel of the plurality of pixels comprises at least one semiconductor device, and wherein the semiconductor device comprises:

a substrate;

at least one gate electrode;

at least two silicon oxide layers comprises a first silicon oxide layer and a second silicon oxide layer, wherein the first silicon oxide layer is nearer to the substrate than the second silicon oxide layer, and wherein a thickness of the first silicon oxide layer is greater than a thickness of the second silicon oxide layer; and a semiconductor layer disposed between at least a portion of the first silicon oxide layer and at least a portion of the second silicon oxide layer.

* * * * *